United States Patent [19]
Bogoch

[11] Patent Number: 5,866,690
[45] Date of Patent: Feb. 2, 1999

[54] DETECTION OF MALIGNANT TUMOR CELLS

[76] Inventor: Samuel Bogoch, 46 E. 91st St., New York, N.Y. 10028

[21] Appl. No.: 487,345

[22] Filed: Jun. 7, 1995

Related U.S. Application Data

[63] Continuation-in-part of Ser. No. 794,356, Nov. 1, 1985, abandoned.

[51] Int. Cl.[6] .............................. C07K 16/30; C12N 5/08
[52] U.S. Cl. ................... 530/388.15; 530/388.8; 530/388.85; 435/326; 435/366; 435/7.24; 436/548; 536/23.53
[58] Field of Search ............................ 530/388.15, 388.8, 530/388.85; 435/326, 366; 436/548; 536/23.53

[56] References Cited

U.S. PATENT DOCUMENTS

| 4,298,590 | 11/1981 | Bogoch | ..................................... 424/1.1 |
| 4,486,538 | 12/1984 | Bogoch | ................................ 424/1.1 X |

FOREIGN PATENT DOCUMENTS 824262  12/1982  WIPO .

OTHER PUBLICATIONS

Hansson, et al., *J. Exp. Med.*, vol. 158, pp. 616–622, Aug. 1983.

Watson, et al., *J. Immunology*, vol. 130, No. 5, pp. 2442–2447, May 1983.

*Primary Examiner*—Toni R. Scheiner
*Attorney, Agent, or Firm*—Kenyon & Kenyon

[57] ABSTRACT

Described herein is the production of two products which are distinct species of human anti-malignin antibody, and the production of a cell line which has the distinguishing characteristic of manufacturing both species of anti-malignin antibody at different times. These anti-malignin products are useful to detect the presence of cancerous or malignant tumor cells. Additionally, these anti-malignin products preferentially attach to cancerous or malignant tumor cells in cell collections in vitro or in vivo and thus can be detected by any visible or other signal emitter attached to said anti-malignin product. This preferential attachment to malignant tumor cells also makes these products useful for metabolic and therapeutic purposes with or without an attached cytotoxic agent.

57 Claims, 6 Drawing Sheets

DETECTION OF MALIGNANT TUMOR CELLS

This is a continuation-in-part of U.S. Ser. No. 06/794,356 filed Nov. 1, 1985, now abandoned.

THE INVENTION

This invention relates to 1) the production of two products which are distinct species of human anti-malignin antibody, and 2) the production of cells, which have the distinguishing characteristic of manufacturing different species of anti-malignin antibody during different growth phases. The above products, both the antibodies themselves and the cells which produce them, are useful for diagnostic, metabolic and therapeutic purposes.

BACKGROUND OF THE INVENTION

The process of cell fusion to produce hybrids is now a routinely used and accepted procedure (Monoclonal Antibodies, Cesar Milstein, Scientific American, May 1980, pp. 66–74). The production of antibodies by the injection of tumor cells into animals has also been a common procedure in the art for many years. U.S. Pat. No. 4,172,124 issued to Hillary Koprowski and Carlo M. Croce discloses a method of producing antibodies to whole tumor cells. The critical first tumors step of the Koprowski et al. method is to inject whole cells from various tumors into an animal. The present invention does not utilize an injection of whole cells into an animal. Nor does the present invention require the use of an injection of a specific polypeptide composition, malignin, the subject of my U.S. Pat. Nos. 4,195,017 and 4,196,186, into an animal to produce the specific species of a specific antibody, anti-malignin antibody as taught in my U.S. Pat. 4,486,538. Whereas these patents describe the production of polyclonal anti-malignin antibody in mammals and mono-clonal anti-malignin antibody in hybridomas, the anti-malignin antibodies of the present invention are genetically human and monoclonal, but are not the products of hybridomas. In addition to a different mode of production, as will be set forth herein, the present monoclonal antibodies have unique properties, and should therefore be uniquely referred to in order to distinguish them from the anti-malignin antibody which is either polyclonal and produced in vivo in mammals, or monoclonal, but produced by hybridomas, and has different properties: i.e., the present antibodies are free of non-human antigenic determinates or epitopes.

SUMMARY OF THE INVENTION

The cell lines themselves, which have been produced by the present invention have the ability to produce Human Monoclonal Anti-Malignin Antibodies. These cell lines are unique in that a single (monoclonal) line or type of cell with an ability to produce Human Monoclonal Anti-Malignin Antibody has been produced. Further, these novel cell lines can produce Human Monoclonal Anti-Malignin Antibody in perpetuity. This new cell therefore herewith designated Human Monoclonal Anti-Malignin Antibody-Producing-Cells. These new cells have immediate utilities related to the patented utilities of their product antibody, i.e. diagnostic and therapeutic. Thus the earlier patents make clear both in their specifications and their examples the diagnostic use of the antibody to detect the antigen Malignin, or any cell which contain Malignin, or to treat therapeutically (i.e. destroy) such cells, i.e. malignant or cancerous cells through the specific reaction of anti-malignin antibody with its specific antigen, malignin, whether the antigen is in solution or fixed in cells or by attaching a cytotoxic agent to the antibody. (See examples 11, 11A, 12 for the use of the antibody to stain cancer cells specifically in immunofluorescence, and see example 13 for the use of the antibody to identify or attach specifically to cancer cells carrying either a signal-matter for identification and localization of the cancer cells in the body, or carrying an anti-cancer drug or chemical (a cytotoxic agent) to be concentrated in the cancer cell for its destruction, as well as examples 16, 17 where the antibody alone is used to treat (destroy) cancer cells.

Additionally, a human cell producing anti-malignin antibody may be isolated. Preferredly, the human anti-malignin antibody producing cell is a lymphocyte. The human lymphocyte producing anti-malignin antibody may be either splenic or peripheral. Moreover, it is further preferred that the anti-malignin antibody producing lymphocyte cell is treated in a manner effective to increase the anti-malignin antibody producing cell antibody production rate beyond the cell's baseline antibody production rate.

In one embodiment of the present invention, the human lymphocye producing anti-malignin antibodies is treated with a material which stimulates antibody production. In another embodiment of the present invention, the anti-malignin antibody producing lymphocyte is transformed into a cell capable of continuous growth and division. A single transformed anti-malignin antibody producing cell and its progeny constitute a cell line producing monoclonal antibodies.

DETAILED DESCRIPTION OF THE INVENTION

Figure 1:
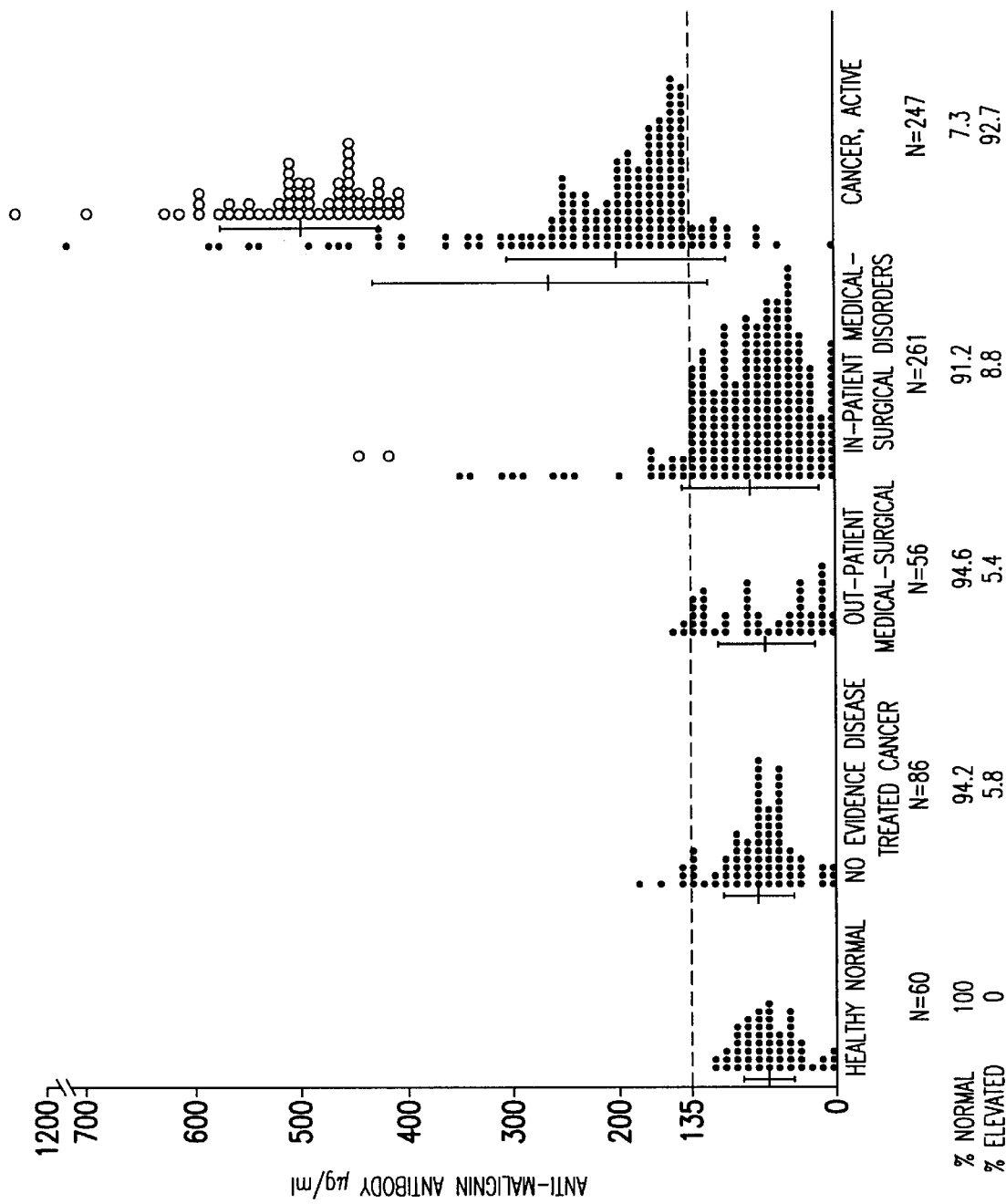
FIG. 1 is a plot of the concentration of anti-malignin antibody in control group subjects and active cancer group subjects.

Two constituent species of anti-malignin antibody were recognized early: 1) Fast Target-attaching-globulin (F-TAG) and 2) Slow Target-attaching-globulin (S-TAG) (Issued U.S. Pat. Nos. 4,195,017 and 4,196,186). F-TAG combines rapidly i.e. in vitro, within 10 minutes with its specific immobilized antigen malignin. S-TAG slowly combines i.e. in vitro within 2 hours, with its specific immobilized antigen malignin (see Examples 10, 10A) U.S. Pat. No. 4,196,186 disclosed a cancer diagnostic test which was based on a determination of the concentration of S-TAG and F-TAG in blood serum of individuals. The disclosed method never yielded either antibody completely free of the other. The present invention discloses the production of unique cell in which produces human F-TAG and human S-TAG at different phases in the cell line's growth cycle.

As summarized above, the ability of the previous polyclonal anti-malignin antibody, which contained both species, to destroy cancer cells specifically (cytotoxicity) was described in U.S. Pat. No. 4,195,017. It was further found that either single species of monoclonal antibody product S-TAG, Monoclonal Anti-Malignin Antibody-Slow (MAMA-S), and F-TAG, Monoclonal Anti-Malignin Antibody—Fast (MAMA-F) preferentially attach to cancer cells, but neither single species will destroy cancer cells. The species of combined human antibody here produced for the first time by monoclonal producer cells, designated HMAMA-FS, as well as an artificial mixture of the two antibodies HMAMA-S and HMAMA-F, preferentially attaches to and destroy cancer cells. The separation of the attachment function from the destruction function of these species of anti-malignin antibody has important applications for diagnosis and treatment (destruction) of cancer.

Careful clinical studies of possible individual patients suffering from cancer has provided unequivocal data (Examples 10A & 10B) that patients who survive longer than one year—13 to 46 months—have higher levels of anti-malignin antibody than those patients who died within one year. Patients with low levels of the antibody were dead within one year. The link between survival and elevated serum levels of anti-malignin antibody suggests therapeutic utility for this antibody. The findings of Example 10A were independently confirmed in a blind test, Example 10B.

Therefore, in light of the clinical studies showing that the serum level of anti-malignin antibody is related to survival, it is important to have a supplemental antibody which is not rejected by the patient's immune system.

The new inventions described in this application, produce a human antibody to the patented product malignin and novel cell lines which are capable of continuous growth and division thereby producing the specific, preferentially-attaching and cancer cell-destroying, human anti-malignin antibodies in virtually limitless quantities. These inventions therefore acquire an added significance as novel therapeutic anti-cancer products.

The novel cell lines of the present invention carry the permanent instruction in their genetic apparatus to manufacture the particular human antibody product. Some of these cell lines also carry the instruction to continue to divide indefinitely. Both of these instructions are seen in the Examples herein. Those familiar with the art will recognize that the particular cellular constituents which carry this genetic information can be isolated and induced to perform their particular functions in the antibody manufacture in vitro, should this transfer be particularly useful. For example, should there by an efficiency, cost or other advantage to doing so, the nucleic acid of the producer cell which carries the specific information for manufacturing human monoclonal anti-malignin antibody can now be removed and isolated from the other cellular constituents and inserted into another type of cell, such as a bacterial, which might divide more quickly, be less susceptible to contamination during bulk manufacture or less costly to continuously maintain in the laboratory.

Anti-malignin antibody reacts specifically immunologically not only with the antigen malignin, but also with the closely structurally related products such as Astrocytin, Recognin L and Recognin M. This present invention therefore continues to be directed to the novel group of compounds, herein termed Recognins. Recognins are made by treating tumor cells or artificial cancer cells and separating the desired products. The Recognins may be used to prepare their Chemoreciprocals, i.e., by contacting the Recognins or the Recognins on a support with body fluids. These Chemoreciprocals are useful for diagnostic and therapeutic purposes, i.e., for diagnosing and treating cancers.

One of the Recognins of the present invention is Astrocytin. Astrocytin is produced from brain tumor tissue, preferably brain glioma tumor tissue. Protein fractions containing the Astrocytin precursor are first extracted from the tissue. A preferred method of accomplishing the extraction is to treat the tissue with a neutral buffer under conditions of homogenization or other techniques to disrupt the cells and tissues in order to solubilize protein fractions which contain the Astrocytin precursor.

At this point, the Astrocytin precursor is still bound to many large molecular weight substances including protein, glycoproteins, lipo-proteins, nucleic acids, then separated from the resultant tissue extract. The extract solution from the tissue is then clarified to remove insoluble particles. The low molecular weight contaminants are then removed from the resultant solution, by a preevaporation concentration technique. The solution which is obtained is then treated to cleave Astrocytin precursor from other contaminants in order to obtain the protein fraction having a pK range between 1 and 4. Thus, for example, the solution is placed on a chromatographic column and eluted with increasing acidic solvents. All of the fractions which are eluted in the neutral or acid range down to pK 4 are discarded and those fractions with pK range 1–4 are collected. The eluate is then treated to obtain a product having a molecular weight of about 8,000. This is accomplished, for example, by first filtering the material to remove low-molecular-weight substances, i.e., those below 1,000 molecular weight, and filtering again to remove those above 25,000. The fraction having a molecular weight between 1,000 and 25,000 is then further treated, i.e., by thin layer gel (TLG) chromatography, to obtain Astrocytin.

Thus Astrocytin may be produced by extracting brain glioma tumor tissue with a neutral buffer, by repeated homogenization and high speed centrifugation, separating from the resulting extract the fraction having a pK range of from about 1 to 4, separating from said fraction the substances having a high molecular weight, i.e., up to about 230,000, and isolating therefrom the product Astrocytin having a molecular weight of about 8,000.

The product Astrocytin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 $\mu$m and having a molecular weight of about 8,000.

Astrocytin is also characterized by having a very high percentage of residues of glutamic acid and aspartic acid and a very high ratio of these acids to histidine. A further analysis of Astrocytin is provided below.

In a manner similar to that described above, another Recognin, called Malignin, is produced from artificial cancer cells, i.e., cancer cells grown in vitro. Malignin has a molecular weight of about 10,000 and similar but distinct amino acid residue composition to Astrocytin, i.e., high amounts of glutaminic acid and aspartic acid and high ratios of these acids to histidine. A further analysis of Malignin is provided below.

Thus, Malignin can be produced by extracting artificial cancer cells grown in culture with a neutral buffer by repeated homogenization and high speed centrifugation, separating from the resulting extract the fraction having a pK range of about 1 to 4, separating from said fraction the substances having a high molecular weight, i.e. up to about 230,000, and isolating therefrom the product having a molecular weight of about 10,000.

Malignin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length 280 mµ and having a molecular weight of about 10,000.

Recognins are further characterized by being capable of complexing with bromoacetylcellulose to form bromoacetyl-cellulose-Recognin and producing the specific antibodies Anti-Recognin upon injection into mammals, said Anti-Recognin being toxic to brain-tumor cells in vitro and producing fluorescence of glioma cells when coupled with fluorescein, as described in further detail below.

Recognins, such as Astrocytin, Malignin and similar substances are useful as products which may be introduced into a biological system to reduce foreign reactions, such as by coating a material with a Recognin. A further example may be to introduce a Recognin in order to produce the Chemoreciprocals in the biological system. They may also be used nutritionally to encourage the growth of a particular biological system of which they are a part. A further utility of Recognin is the production of Target reagents which comprise the complexes of the Recognin with a carrier to facilitate its applicability in biological systems. Thus, for example, the complex conveys the physical-chemical characteristics of the Recognin itself. The carrier should be selected from those which form a complex with the Recognin and which are substantially biologically inert.

Any substance known in the art which will form a stable complex with polypeptides or proteins may be useful for complexing with the Recognin. An example is a cellulose-based material, such as bromoacetyl-cellulose. In addition to being inert to the biological system, the carrier should be one that does not alter the specific physical-chemical properties of the Recognin which are useful for the purposes set forth herein.

The complexes of the Recognin and its carrier are useful for producing, separating and identifying its chemoreciprocal in any biological system with which it is brought into contact. The Recognin-carrier complex is also useful for stimulating the production of its chemoreciprocal precursor in any biological system into which it is introduced.

One class of Chemoreciprocals are the anti-Recognins, i.e., anti-Astrocytin and anti-Malignin. These may be made by injecting the Recognin into a biological system. An immunologically effective dose of Recognin is brought into contact with bodily tissues or fluids in a manner which induces an antibody response in accordance with techniques known in the art for producing antibodies. The anti-Recognins may be used for the delivery of materials such as diagnostic, nutritional and therapeutic agents to specific cells or sites in a biological system which comprises introducing said agent in complexed form with the anti-Recognin into the biological system. The anti-Recognins are also useful for diagnosing the presence of tumor cells in a histology section, by applying the Anti-Recognin conjugated with a labeling substance such as dyes and radio-active substances to said section, whereby staining or radio-active labeling occurs only with tumor cells. Yet another use for anti-Recognins is for increasing the yield of other useful Chemoreciprocal products (such as TAG, described below) from a mammal which comprises injecting an immunologically effective dose of Recognin into the mammal, or other biological system.

Another class of Chemoreciprocals is Target reagents complexed with their chemoreciprocals. For example, the Target product of Astrocytin complexed with a carrier such as bromoacetylcellulose is brought into contact with anti-Astrocytin. This type of compound may be complexed with and used for the delivery of diagnostic, nutritional and therapeutic agents to specific cells or sites in a biological system. These compounds may also be used for purification procedures. For example, Anti-Astrocytin may be made by the decomplexing of Bromoacetylcellulose-Astrocytin-Anti-Astrocytin by hydrolytic treatment with an acid or proteinase enzyme. Target reagents are also useful for increasing the amount of TAG products (described below) in a biological system, such as by bringing an immunologically effective dose of Target into contact with bodily tissues or fluids.

Additional Chemoreciprocals are TAG reagents (e.g., Target-Attaching-Globulins). The TAG products are produced by bringing Target reagents into contact with body fluids for varying periods of time to form a complex and cleaving TAG therefrom. Two useful embodiments are S-TAG and F-TAG.

A process for producing S-TAG. (Slow-Target-Attaching-Globulin) comprises reacting blood serum or other body fluid with Target (i.e., Bromoacetylcellulose-Malignin) for approximately two hours or more at a low temperature, e.g., about 4° C., and cleaving S-TAG from the resulting material, e.g, with dilute acid for approximately two hours at a temperature of about 37° C. The product S-TAG prepared in accordance with this process characterized by being soluble in aqueous buffered solutions, forming a single line precipitate with its corresponding Recognin in Ouchterlony gel diffusion tests, being non-dialyzable in cellophane membranes, being retained by millipore filters which retain molecules over 10,000 molecular weight, having molecular weights in different states of aggregation as determined by thin layer gel chromatography of approximately 50,000, and multiples thereof into the macroglobulin range and having a spectrophotometer absorption peak wave length of 280 mµ.

A process for producing F-TAG (Fast-Target-Attaching-Globulin) comprises reacting blood serum or other body fluid with Target (i.e., Bromoacetylcellulose-Malignin) for approximately 10 minutes at a low temperature, e.g., about 4° C., and cleaving F-TAG from the resulting material, e.g., with dilute acid for approximately two hours at a temperature of about 37° C. The product F-TAG prepared in accordance with this process is characterized by being soluble an aqueous buffered solutions, forming a single line precipitate with its corresponding Recognin in Ouchterlony gel diffusion tests, being non-dialyzable in cellophane membranes, being retained by millipore filters which retain molecules over 25,000 molecular weight, having molecular weights in different states of aggregation as determined by thin layer gel chromatography of approximately 50,000, and multiples thereof into the macroglobulin range and having a spectrophotometer absorption peak wave length of 280 mµ.

TAG products are useful for detecting cancer tumors in living mammals by determining the concentration of S-TAG and F-TAG produced by a known volume of the mammal's blood serum or other body fluid and correlating this concentration with amounts determined to be indicative of cancer. TAG products are also useful for diagnosing the presence of tumor cells in a histology section, which comprises applying TAG conjugated with a labeling substance such as dyes and radioactive substances, to said section, whereby staining or radioactive labeling occurs only with tumor cells. TAG products additionally have been found to be cytotoxic to tumor cells. TAG products are also useful for directing the delivery of diagnostic, nutritional and therapeutic agents to specific cells or sites by introducing said agents in complexed form with the TAG product.

Normal cell division in plants or animals is restricted or inhibited when the cells come to occupy fully a particular space. The mechanisms (a) by which normal cells "recognize" that they have filled the space available to them, and (b) by which the operation of this recognition mechanism in turn inhibits cell division, have both been unknown. The inventor has produced a group of compounds whose precursors are increased in concentration when normal recognition and learning occur, and which relate to recognition and learning in particles and cells, and with the connection of cells to each other. These compounds are termed RECOGNINS by the inventor. By attempting to produce these compounds from normal cancer cells, the inventor has discovered that they are absent as such, and that changes in their molecular structure have occurred at the same time that the cancer cells have lost their ability (a) to recognize that they have filled their normal volume, and/or (b) to stop dividing when they have filled their normal volume.

The inventor has discovered novel compounds and methods for producing such compounds. These new compounds are termed RECOGNINS by the inventor. RECOGNINS are novel compounds which have physicochemical characteristics which mimic those configurations characteristic of cancer cells in terms of their failure to recognize and stop cell division. The use of RECOGNINS goes beyond insight into the cancer mechanism, for immediate products and methods are thereby provided which are useful in the diagnosis and treatment of cancer, and for its prevention.

I have discovered methods by which artificially cultured cells can be used to produce MALIGNINS for the first time. One advantage of the methods disclosed herein is that MALIGNINS and new products from them can now be manufactured efficiently in virtually limitless quantities.

This invention transcends the field of cancer research and is immediately applicable to any and all biological systems in which it is desired to influence all growth and metabolism. Thus by the manufacture of the particular compound or compounds of appropriate cell type in artificial culture, and the further manufacture of products from these substances, specific influence may for the first time be brought to bear on any tissue, cell, cell organelle, sub-organelle molecule or molecular aggregate in any living system. Thus specific nutritional influences at critical times in development, specific diagnostic, preventative and treatment methods, and the construction of artificial bioelectrical systems (as in tissue or organ transplants) can all be affected for the first time. These artificial bioelectrical systems can now be made to bear the characteristics of the specific RECOGNIN, MALIGNIN or their CHEMORECIPROCALS of the normal tissue or component which they will neighbor and thus avoid being "recognized" as "foreign" and thus avoid the reactions to alien substances, including rejection.

Another aspect of this invention is the production of a valuable specific antibody-like product (Anti-Astrocytin) to a specific brain product (Astrocytin), permitting the use of this antibody-like product to specifically complex with and, as a specific delivery vehicle to, specific points in the nervous system of all species. MALIGNINS and ASTROCYTIN are RECOGNINS.

Still another aspect of this invention is the production from biological fluids of two new products, TARGET-ATTACHING-GLOBULINS (TAG), which are so named because they are produced by two reactions, the first reacting biological fluids with a synthetic complex containing physicochemical configurations which mimic those of the MALIGNINS and called TARGET, the second, cleaving the specific TAG from the complex, and by the measure of the TAG so produced obtaining a quantitative indication from the biological fluids of living organisms whether these is present a tumor in that organism; hence a diagnostic test for tumors. Because TAG products and ANTI-MALIGNIN are physicochemically complimentary to MALIGNINS, they are termed CHEMORECIPROCALS.

I have further discovered that two quantitatively and qualitatively distinct TAG products can be produced depending upon the time permitted for the reaction of serum with the specific TARGET reagent used, and depending upon the time permitted for the cleavage of the product which has been complexed.

After examing the amounts of these products which could be produced from a number of different individuals with brain tumors and various other medical disorders, as well as in those with no apparent disease process, it became apparent that the amounts of these two new products which could be produced in a given individual was indicative of whether that individual had a malignant tumor, hence a serum diagnostic test for malignant tumors, the first to my knowledge.

The utility of these new products, in addition to their use to diagnose from serum and other biological fluids the presence of brain and other tumors, is illustrated by the demonstration that TAG and anti-RECOGNIN compounds attach to glial tumor cells preferentially in histological section of brain tumor and surrounding tissue removed at surgery of the brain tumor. This preferential labelling by TAG and Anti-RECOGNINS of tumor cells is demonstrated through standard immunofluorescent techniques. Thus a new method is also available for determining through histological examination with a new degree of certainty whether tumor cells are present in the tissue removed, and whether these tumor cells have penetrated to the very edges of the tissue removed indicating the likelihood that tumor still remains in the brain or other organ, or that tumor cells are absent from the periphery of the tissue removed, indicating the possibility that all of the tumor has been removed from the brain or other organ. In addition, TAG and Anti-RECOGNINS produced as described have been found to be cytotoxic for glioma brain tumor cells grown in tissue culture in vitro. This high affinity for tumor cells in another medium, here grown in tissue culture, is further evidence of the specific-coupling potential of the new product TAG, and explains the adoption of the name TARGET-ATTACHING-GLOBULINS (TAG) as do TAG's properties in regard to the synthetic product TARGET, and to tumor cells in histological section. Further, the cytotoxicity of TAG and anti-RECOGNINS for tumor cells provides an additional new diagnostic test for serum of patients who are suspected of suffering from a tumor. Thus, for example, the serum or other body fluid of these patients is reacted with TARGET to produce TAG and the product TAG is tested in tissue culture growths of tumor cells for cytotoxicity. Both the concentration of TAG and the degree of cytotoxicity manifested by the TAG which can be produced from a given individual's serum may be not only diagnostic but also of value in tracing the course of the disorder preoperatively and postoperatively in a given patient. Coupling of radioactive and dye tracers to TAG provides new TAG products which are useful in vivo in the diagnosis of tumors and in their exact localization. Thus the infection of suitably labelled TAG either intraarterially or intravenously, into the cerebrospinal fluid, or directly into brain tissue or its cavities, permits the demonstration by radioactive means, or by visualization of the coupled dye, of the presence of a brain tumor, for it is only to the tumor cells that the TAG specifically attaches. Further, this method permits the precise visualization of the location of the brain tumor. This can be seen to be an improvement of this in vivo diagnostic method using anti-ASTROCYTIN produced in rabbit blood to label the brain tumor, because the use of TAG produced from human serum avoids the possibility of foreign protein reactions. Since TAG and anti-RECOGNINS have the chemical specificity which permits preferential attachment to ASTROCYTIN precursor containing tumor cells both in vitro and in vivo, these products may also be used therapeutically, as well as diagnostically, when coupled, e.g., with radioactive, proton capture agents, or other toxic physical or chemical agents, so that these toxic substances may be localized preferentially through these compounds' specificity of attachment in the tumor cells as compared to their neighboring normal cells. This selectivity is universally recognized as the crucial, or at least one crucial factor for achieving effective chemical or physical therapy of tumors, and a factor which has hitherto not been achieved. Thus TAG has demonstrated efficacy in attaching preferentially to the tumor cells, and has the properties as a new therapeutic product for these reasons.

In the serum of patients with malignant tumors, as will be seen in the examples below, one type of TAG, SLOW-TAG (S-TAG) as distinguished from FAST-TAG (F-TAG), can be produced in relatively greater amounts from a given volume of serum than in patients without such tumors. This suggests that either one of TAG's naturally occuring precursors (P-TAG) is increased in concentration or that other factors exist which favor the relative in vitro production of S-TAG over F-TAG.

The possible relationship of the function of the actual synthetic products TARGET and TAG to their precursors, and in turn to functions of postulated but not demonstrated cell "antigens" and circulating "antibodies" to them which may exist in vivo has yet to be elucidated. Thus for example, in antibody-like fashion, F-TAG and S-TAG produce single discrete lines of reaction with ASTROCYTIN in Ouchterlony get diffusion, and the injection of TARGET in rabbits induces en increase in the yield of TAG products from rabbit serum after reacting with TARGET. The finding that there may be a normal level of a precursor resembling circulating antibody to a cell antigen which is hidden in the non-dividing cell raises a question as to the possible function of the pair. It is here proposed that TAG precursor (P-TAG) and TARGET-like substances exist in vivo which function in the control of cell proliferation and cell death. Thus, for example, the exposure of a cell constituent which normally is not directly exposed to serum proteins may occur during cell division. The exposure of this cell constituent could result in that constituent becoming converted to a TARGET-like substance to which the attachment of a P-TAG like molecules from serum may then occur, which would stimulate cell divisions or inhibit it. Alternatively, a non-dividing cell which is injured or malfunctioning may expose a TARGET-like substance to which the attachment of P-TAG like molecules may be reparative. However, under certain cell conditions the attachment of P-TAG like molecules may induce the destruction of the cell (e.g. ANTI-GLIOMA-TAG synthetically produced as here described is markedly cytotoxic to glioma tumor cells growing in tissue culture). This could thus represent a mirror of a normal mechanism for the control of cell division, and for either the repair or the removal of individual cells in the body throughout the life of the organism. If the exposure of cell constituents is abnormally increased so that abnormally large amounts of cell TARGET-like substances are formed, as may occur in rapidly dividing cancer cells such as in brain gliomas, an increase in the concentration of one type of serum P-TAG relative to another may be induced.

Whatever the actual function of the precursors, the increase in the relative amount of predominately one type of TAG, SLOW-TAG (S-TAG) which can be produced in vitro by the methods here described from the serum of patients with malignant tumors is the basis of the serum diagnostic test described in the examples which follow.

The ability to produce specific human monoclonal species for S-TAG and F-TAG by means of new cells as described herein, has permitted the preparation of human TAG molecules. Thus whereas the earlier TAG products had the properties of preferential attachment to malignant cells and the cytotoxic property wherein the malignant cell is destroyed, the presently described process produces human forms of TAG, MAMA-A and MAMA-B. The human forms of TAG, MAMA-A and MAMA-B each demonstrates a preferential attachment and specific fluorescence with malignant cells, but are not cytotoxic. However, a mixture of MAMA-A and MAMA-B produces both flurescence and cytotoxicity. The separation of diagnostic and therepeutic uses is thus possible for the first time.

The ability to produce human S-TAG, and F-TAG as herein described has permitted the development TAG molecules that do not possess nonhuman antigenic domains and therefore should not be rejected by anti-nonhuman peptide antibodies. These new human anti-malignin antibodies can therefore be used in both in vivo and in vitro applications.

The following examples illustrate the invention.

EXAMPLE 1

Production of Crude ASTROCYTIN-Precursor-Containing Fraction.

Human brain glioma tumor tissue, removed at surgery, is dissected free as possible of surface blood vessels and normal brain tissue. For a typical amount of dissected tumor tissue of 11 grams, the tissue is weighed into six 1.5 g. and two 1.0 g. aliquots. Each aliquot is then treated as follows.

Each aliquot is homogenized in neutral buffer solution by sonification or other mechanical means. For example, each aliquot is homogenized in 100 cc per g. of tissue of 0.005M phosphate buffer solution, pH 7, in a Waring blender. Homogenization should be done in the cold to prevent denaturation of proteins. For example, the blender should be precooled in a cold room at 0°–5° C. and operated for about only three minutes.

The homogenate is then centrifuged for clarification, for example at 80,000 times gravity for 30 minutes in a refrigerated ultracentrifuge. The soluble supernatant is decanted and kept in the cold. The insoluble residue is rehomogenized with a further 100 cc of neutral buffer and centrifuged as before, and the second soluble extract combined with the first. Best yields are obtained when this procedure of homogenization and centrifugation is repeated until less than 50 micrograms of protein per ml. of solution are obtained in the supernate. With most tissues this is accomplished by the fifth extraction.

The solutions thus obtained are combined and concentrated by preevaporation with subsequent dialysis, such as by dialysis against 0.005M phosphate buffer in the cold to produce a volume of 15 ml. The volume of this solution is noted, an aliquot is taken for total protein analysis, and the remainder is fractionated to obtain the protein fraction having a pK range between 1 and 4. The preferred method of fractionation is chromatography as follows.

The solution is fractionated in the cold room (4° C.) on a DEAE cellulose (Cellex-D) column 2.5×11.0 cm., which has been equilibrated with 0.005M sodium phosphate buffer. Stepwise eluting solvent changes are made with the following solvents solution): Solution (1) 4.04 g. $NaH_2PO_4$ and 6.50 g. $Na_2HPO_4$ are dissolved in 15 litres of distilled $H_2O$ (0.005 molar, pH 7); Solution (2) 8.57 g. $NaH_2PO_4$ is dissolved in 2480 ml. of distilled $H_2O$; Solution (3) 17.1 g. of $NaH_2PO_4$ is dissolved in 2480 ml. of distilled $H_2O$, (0.05 molar, pH 4.7); Solution (4) 59.65 g. of $NaH_2PO_4$ is dissolved in 2470 ml. distilled $H_2O$ (0.175 molar); Solution (5) 101.6 g. of $NaH_2PO_4$ is dissolved in 2455 ml. distilled $H_2O$ (0.3 molar, pH 4.3; Solution (6) 340.2 g. of $NaH_2PO_4$ is dissolved in 2465 ml. of distilled $H_2O$ (1.0 molar, pH 4.1); Solution (7) 283.64 g. of 80% phosphoric acid ($H_3PO_4$) is made up in 2460 ml. of distilled $H_2O$ (1.0 molar, pH 1.0).

Add nervous tissue extract, 6 to 10 ml. volume. Let it pass into column. Then overlay with Solution (1) and attach a reservoir of 300 ml. of Solution (1) to drip by gravity onto the column. Three ml. aliquots of effluent are collected by means of an automatic fraction collector The subsequent eluting solutions are exchanged stepwise at the following elution tube numbers. Solution (2): at tube 88, bring solution on column to top of resin, then overlay and attach reservoir of 50 ml. of Solution (2); Solution (2): at tube 98, bring solution of column to top of resin, then overlay and attach reservoir of 75 ml. of Solution (3); Solution (4): at tube 114, bring solution on column to top of resin, then overlay and attach reservoir of 150 ml. of Solution (4); Solution (5): at tube 155, bring solution on column to top of resin, then overlay and attach reservoir of 125 ml. of Solution (5); Solution (6): at tube 187, bring solution on column to top of resin, then overlay and attach reservoir of 175 ml. of Solution (7); continue eluting until at tube 260, elution is complete. Use freshly prepared resin for every new volume of tissue extract. Each effluent tube is quantitatively analyzed for protein. The eluates in the tube numbers 212 to 230 are combined, and contain the crude products a from which ASTROCYTIN will be produced.

While date has been published on this crude material, called fraction 10B in the past, (*Protein Metabolism of the Nervous System*, pp. 555–569 (Plenum Press, 1970); *Journal of Neurosurgery*, Vol. 33, pp. 281–286(September, 1970) the cleavage from fraction 10B can be prepared as a product in amounts between 0.1 and 10 mg. per gm. of original fresh nervous system tissue from which it was obtained. In addition to an ASTROCYTIN-precursor it contains varying amounts of covalently bound carbohydrate residues including a number of hexoses, namely glucose, galactose, mannose; hexosamines, including glucosamine, galactosamine and mannosamine; and occasionally other sugars, such as fucose, ribose and perhaps rhamnose. It also contains large molecular weight protein products, several lipids and nucleic acids.

EXAMPLE 2

Production of Purified ASTROCYTIN from Crude ASTROCYTIN-Precursor-Containing Fraction.

The ASTROCYTIN-Precursor-Containing fraction is further isolated from contaminants. In the preferred embodiments, the material from Example 1 is chromatograted on Sephadex G-50 resin with a typical column of 40 cm. long, 2.5 cm. diameter, and 196 ml. volume. The pressure used is 40 mm. Hg.; the flow rate is 35 ml. per hour, and the buffer is 0.05 molar phosphate buffer solution, pH 7.2. The first (flow-through) peak contains ASTROCYTIN-Precursor together with impurities, whereas subsequent peaks contain only impurities.

In the preferred embodiment, the products in the above first flow-through peak are then concentrated on Sephadex G-15, then passed onto a column of Cellex-D with the same solutions, (1) through (7) as Example 1, and the same elution steps as performed in Example 1. The product ASTROCYTIN is present as a sharp peak in the same tubes (numbers 212–230) as before, thus maintaining its behavior on Cellex-D chromatography without the presence of a large number of contaminants.

Low molecular weight contaminants may then be removed by techniques so known to the art, such as millipore disc filtration. In the preferred method, the product ASTROCYTIN is freed of salt and other small molecular weight contaminants by filtration through Millipore Pellicon Disc No. 1000, 13 mm., which retains substances of molecular weight greater than 1000 and permits to pass through those of molecular weight less than 1000. The product ASTROCYTIN remains on the Pellicon Disc, and is recovered from it by washing with Solution (1) of Example 1.

ASTROCYTIN is then obtained by isolating the compound having a molecular weight of about 8000 from the above solution. A preferred method uses thin layer gel (TLG) chromatograph as follows:

The apparatus used is the commercially available one designed by Bochringer Mannheim GmbH; Pharmacia Fine Chemicals and CAMAG (Switzerland). The resin 2.5 g. of Sephadex G-200 superfine is prepared in 85 ml. of 0.5M. NaCl in 0.02M. $Na_2HPO_4KH_2PO_4$ Phosphate Buffer pH 6.8 (6.6–7.0). Allow to swell two or three days at room temperature with occasional gentle mixing. (Magnetic and other stirrers should not be used.) The swollen gel is stabilized for three weeks at refrigerator temperature; however, bacterial and fungal growth may interfere with the swollen gel. If the gel is to be kept for longer periods of time, a small amount of a bacteriostatic agent should be added (sodium azide 0.02%) 2.5 g. of dry gel are used to make two 20×20 cm. glass plates of 0.5 mm. thick. The plates are either allowed to dry at room temperature for 10 minutes and transferred to a moist chamber where they can be stored for about two weeks, or they are used immediately after appropriate pre-equilibration. (Usually during the night for a minimum of 12 hours.) The main function of equilibration is to normalize the ratio between the stationary and mobile phase volumes. With the pre-equilibrated plates in a horizontal position, substances to be determined are applied with micropipettes as spots or as a streak at the start line. 10 ml. to 20 ml. of 0.2–2% protein solution is placed on the edge of a microscopic cover slide (18×18 mm.) and held against the gel surface. In a few seconds the solution will soak into the gel. All samples are first prepared on the cover slides and then quickly applied. If not enough material is used, it is difficult to locate individual spots after separation. If too much material is applied no defined separation occurs. The samples are diluted with buffer for easier handling and the separation of samples is carried in a descending technique with the plate at an angle of 22°. The flow rate of about 1–2 cm/hour is most suitable. Marker substances (such as cytochrome C, haemoglobin, myoglobin or bromophenol Blue labeled albumin) are applied at different positions across the plate to give a check on possible variation of flow across the plate and also to serve as reference proteins for calculation of relative distance (mobility) of unknowns. After application of samples, the plates are replaced in the apparatus and the paper wick pushed slightly downwards to ensure good contact with the gel layer. The paper wick must not drip. Excess moisture is wiped off. The liquid solvent in the reservoir is kept constant at 1 cm. from the upper end of the vessel. The runs are usually completed in 4 to 7 hours depending on the progress of separation. With colored substances separation follows directly. The separated spots of protein are easily made visible by transferring them to a paper sheet replica of TLG plate after the chromatographic separation has been completed, and by staining them on the prewashed methanol $+H_2O+$acetic acid–90:5:5, for 48 hours. The paper sheet is 3 mm. filter paper. A sheet of paper 20×18 cm. is placed over the gel layer and pressed (rolled) just enough to ensure contact with the gel. Care is taken not to trap air under the paper (replica) and not to disturb the gel layer. The liquid phase is soaked off from the gel layer by the paper and removed after about one minute, immediately dried in an oven at a 60° temperature for 15 minutes and stained in the normal way with any of the routine staining procedures. Staining is performed by spraying the replica-paper with 0.03% diazotized sulfanilic acid in 10% Sodium Carbonate (Pauley's Reagent). Staining can also be accomplished with a saturated solution of Amido Black in Methanol-Acetic Acid (90:10 v/v is used); the staining time is 5–10 minutes. For destaining, rinse with two volumes of the 90:10 methanol and acetic acid solution mixed with one volume of $H_2O$. It is difficult to obtain low background staining without very extensive washing. The plates themselves may also be dried at about 60° C. (in an oven with air circulation) but only if the ASTROCYTIN is to be stained. For isolation purposes, the plate should only be air dried at room temperature. Over-heating can lead to cracking, but this can usually be avoided with a 50°–60° temperature which dries a sephadex G-200 plate in 15–30 minutes. The dry plates are allowed to swell for 10 minutes in a mixture of methanol $+H_2O$ +-acetic said (75:20:5) and stained in a saturated Amido Black in the same solvent system for five hours and subsequently washed by bathing for two hours in the same solvent before they are dried. For molecular weight determinations the distance from the starting line to the middle of each zone is measured with an accuracy of 0.05 mm. either directly on the print (replica) or on the densitogram. The result is expressed by the $R_m$ value defined as the ratio of the migration distance of the tested protein ($d_p$) to that of cytochrome C or myoglobin ($d_m$) which is used as the reference protein: Relating migration distance of tested substance to standard is the formula ($-R_m={^d}p/{^d}m$). A straight calibration line is obtained by plotting the logarithm of the molecular weight of the standards used against the $R_m$. From this line the molecular weight of the unknown protein can be obtained. For most exact results six equal parts of the protein sample solution with standard, in this case, Cytochrome C, before applying to the plate. Byt the above TLG procedure the product ASTROCYTIN is observed as a discrete spot at a distance of approximately 0.83±0.02 with reference to the standard Cytochrome C, yielding an approximate molecular weight of 8000 for ASTROCYTIN. Several discrete products are separated in this procedure from ASTROCYTIN on the basis of slight differences in chemical structure and large differences in molecular weight. Thus, three products carried as contaminants to this point with molecular weight of approximately 64,000, 148,000 and 230,000, and one occasionally of molecular weight 32,000, have been detected and removed by the TLG methods described above. The product is ASTROCYTIN is aspirated with the gel in which it is contained, in dry form, dissolved in Solution (1) and freed of resin by centrifugation or other similar means.

The product ASTROCYTIN which has been produced at this stage is soluble in distilled water, soluble at neutral and acid pH, and insoluble at alkaline pH and has a spectrophotometric absorption peak wavelength of 280 m$\mu$. It is a polypeptide with molecular weight, as stated above, of approximately 8000. Its covalently linked amino acids are shown by hydrolysis with 6N HCl then quantitative automatic determination to have the following average composition of amino acids:

|  | Approximate Number of Residues |
|---|---|
| Aspartic acid | 9 |
| Threonine | 5 |
| Serine | 6 |
| Glutamic acid | 13 |
| Proline | 4 |
| Clycine | 6 |
| Alanine | 9 |
| Valine |  |
| 1/2 Cystine | 2 |
| Methionine | 1 |
| Isoleucine | 2 |
| Leucine | 8 |
| Tyrosine | 2 |
| Phenylalanine |  |
| Lysine | 8 |
| Histidine | 2 |
| Arginine | 4 |
| Approximate Total | 88 |

Cysteic acid, hydroxyproline, norleucine, ammonia, isodesmosine, desmosine, hydroxylysine, lysinonorleucine and gamma-aminobutyric acid are all absent in detectable amounts, but a trace of glucosamine may be present.

From 11 grams of the starting brain tumor tissue in EXAMPLE 1, approximately 3 mg. of purified ASTROCYTIN is produced by the above methods.

EXAMPLE 3

Production of MALIGNIN-Precursor in Artificial Cancer Cell Culture.

Generally, sterile technique is scrupulously maintained.

All solutions (e.g. Hank's Balanced Salt (BSS), F-10 Nutrient medium, fetal calf serum, trypsin solution) are incubated at about 35° C. in a water bath for approximately 20 minutes or more before use.

Cells are removed from tumor tissue and grown in vitro for many generations using a suitable medium, such as described below. Pre-rinse beakers to be used with a sterilizing solution, for example, 12-proponal plus Amphyl or creoline solution.

In the preferred embodiment, the artificial cancer cells (i.e., cells grown in vitro for many generations) are grown in 250 ml. flasks. The liquid medium in which the cells are growing is discharged into the pre-rinsed beakers. The cells are then washed gently with 5–10 ml. of Hank's BSS or other similar solution for about 30 seconds. Avoid agitation. All walls and surfaces are washed. The solution is clarified of cells by centrifugation in the cold from 10 minutes at 3,000 rpm. The medium is poured into a beaker as above. Add a small amount of buffered proteinase enzyme solution and rinse quickly to avoid digestion of the cells. In the preferred method, 1–2 ml. of trypsin solution (EDTA) is added and rinsed for only 10 seconds. Pour off the trypsin solution.

Add a similar volume of fresh trypsin solution and incubate until the cells are seen to be separated from the walls of the chamber through microscopic observation. This usually requires 5–10 minutes. Add a suitable growth medium, such as 50 ml. of a solution of 7–10 percent solution of fetal calf serum in 100 ml. of F-10 Nutrient medium.

Twenty-five ml. of the fresh medium with cells is transferred to a new growth chamber for propagation and the remaining 25 ml. is kept in the first chamber for propagation. Both chambers are placed in an incubator at 35° C. for approximately seven days. By the procedure of this Example to this point, an artificial cancer cell culture is divided into two fresh cultures approximately every seven days. This entire procedure may be repeated as often as desired, at approximately seven-day intervals, for each growth chamber. Thus, the number of cells growing in vitro may be doubled approximately every seven days.

The cells may be extracted for the production of MALIGNIN after approximately seven days of growth. For example, cells growing in each 250 ml. growth chamber as described above, may be recovered as follows.

The medium is transferred to a centrifuge tube and centrifuged at 3,000 rpm in the cold for 10 minutes. The medium is discarded. The cells remaining in the growth chamber are scraped from the chamber walls and washed into the centrifuge tubes with neutral buffer solution. The cells are washed twice with neutral buffer solution, centrifuged again at 3,000 rpm in the cold, and the medium is discarded. The washed cells are suspended in 10 ml. of neutral phosphate buffer until ready for extraction of crude MALIGNIN-Precursor-Containing fraction.

EXAMPLE 4

Production of Crude MALIGNIN-Precursor-Containing Fraction.

Washed cells suspended in neutral buffer from EXAMPLE 3 are mechanically disrupted under conditions which avoid denaturation of most proteins. In the preferred method, the washed cells are treated in the cold with a sonifier for 20 seconds.

After sonification the cell residues are centrifuged at 30,000 rpm for 30 minutes and the supernatant decanted. Ten ml. aliquots of buffer solution are used to wash remaining cells from the chamber and these are added to the remaining cell residues. Sonify and centrifuge as above and combine the supernatants. Repeat the process once more.

The combined supernatant is perevaporated to reduce the approximate 30. ml. volume to about 6–7 ml. An aliquot is taken for total protein analysis and the remainder is fractionated according to the methods of EXAMPLE 1 for ASTROCYTIN Precursor.

EXAMPLE 5

Production of Purified MALIGNIN Product from Crude MALIGNIN-containing Fraction.

The product MALIGNIN is further isolated from contaminants by the methods of EXAMPLE 2 for ASTROCYTIN.

In the TLG step of the preferred embodiment, the product MALIGNIN is observed as a discrete spot at a distance of approximately 0.91±0.02 with reference to the standard cytochrome C, yielding an approximate molecular weight of 10,000 for MALIGNIN.

The product MALIGNIN which has been produced at this stage is soluble in distilled water, soluble at neutral or acid pH, and insoluble at alkaline pH and having a spectrophotometric absorption peak of 280 m$\mu$. It is a polypeptide with molecular weight of approximately 10,000. Its covalently linked amino acids are shown by hydrolysis with 6N HCl then quantitative determination to have the following average composition of amino acids:

|  | Approximate Number of Residues |
|---|---|
| Aspartic Acid | 9 |
| Threonine | 5 |
| Serine | 5 |
| Glutamic Acid | 13 |
| Proline | 4 |
| Glyine | 6 |
| Alanine | 7 |
| Valine | 6 |
| 1/2 Cystine | 1 |
| Methionlne | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| Approximate Total | 89 | the amino acids cysteic acid, hydroxyproline, norleucine, ammonia, isodesmosine, desmosine, hydroxylysine, lysinonorleucine and gamma-aminobutyric acid being absent in detectable amounts.

A typical yield of pure MALIGNIN from twelve 250 ml. reaction chambers of EXAMPLE 3 together is approximately 1 mg. of MALIGNIN.

EXAMPLE 6

Hydrolytic Cleavage of RECOGNINS.

A solution of RECOGNIN, in this case either Astrocytin or Malignin at pH between 1 and 2 is allowed to stand in the cold. After 7 to 14 days, TLG chromatography shows the product to have been reduced in molecular weight by approximately 200. When the solution is allowed to stand longer, further units of approximately 200 molecular weight are cleaved every 7 to 10 days. Thus with Astrocytin the molecular weight is reduced from 8,000, and with MALIGNIN the molecular weight is reduced from 10,000, in each case by units of approximately 200 sequentially.

The physicochemical specificities of ASTROCYTIN are retained by each product down to approximately 4,000 molecular weight. The physicochemical specificities of Malignin are retained by each product down to approximately 5,000 molecular weight. This is shown by Ouchterlony gel diffusion tests against Anti-Astrocytin and Anti-Malignin, respectively.

This cleavage can also be accomplished enzymatically, as with trypsin and other proteinases, with similar results.

The molecular weights of these compounds prepared by hydrolytic cleavage of RECOGNINS may be approximately defined by the following formulae:

For products having the physicochemical specificities of Astrocytin; 4000+200x=Y.

For products having the physicochemical specificities of Malignin; 5000+200x=Y wherein Y is the molecular weight of the product and X is an integer from 0 to 19.

EXAMPLE 7

Production of Artificial Tissue or Organ with RECOGNINS

A rigid walled tube of plastic, metal, or other suitable rigid material is dipped in or impregnated with a highly concentrated (i.e., 10 mg./ml.) viscous solution of RECOGNIN, in this case either Astrocytin or Malignin, until all surfaces are fully coated with the RECOGNIN. Alternately, RECOGNIN solution is passed through and around the tube under pressure until all surfaces are fully coated. The tube is then dried in air or in vacuo, or lyophilized. The process of coating is repeated several times in order to build up multiple molecular layers of RECOGNIN coating.

The tube is now ready to be placed in a cavity or in a tissue which contains Astrocytin or Malignin-like precursors in the neighboring tissue or fluid of a living mammal. This artificial tissue or organ may be used to minimize or eliminate reaction which foreign substances without RECOGNIN coating would incite.

Artificial tissues or organs of other geometries may similarly be produced.

EXAMPLE 8

Production of TARGET reagents from RECOGNINS.

ASTROCYTIN, prepared as in EXAMPLE 2 above, or MALIGNIN, prepared as in EXAMPLE 5 above, is complexed with a carrier to produce TARGET reagent.

In the preferred embodiment, ASTROCYTIN or MALIGNIN is dissolved in 0.15M. $NaH_2PO_4$-citrate buffer, pH 4.0. A bromoacetyl-resin, for example bromoacetylcellulose (BAC) having 1.0 to 1.5 milliequivalents Br per gram of cellulose, stored in the cold, is prepared in 0.15M $NaH_2PO_4$ buffer, pH 7.2. Convert the buffer to pH 4 by pouring off the pH 7.2 buffer solution and adding 0.15M $NaH_2PO_4$-citrate buffer, pH 4.0. The ASTROCYTIN or MALIGNIN solution and the BAC solution are stirred together (10:1 BAC to RECOGNIN ratio) for 30 hours at room temperature, then centrifuged.

It is preferred that all sites on the BAC which are available to bind to RECOGNIN be bound. This may be accomplished as follows. The supernatant from the immediately preceding step is lyophilized and the protein content determined to indicate the amount of ASTROCYTIN or MALIGNIN not yet complexed to BAC. The complexed BAC-ASTROCYTIN (or BAC-MALIGNIN) is resuspended in 0.1M bicarbonate buffer pH 8.9, stirred 24 hours at 4° to permit the formation of chemical bonds between the BAC and the ASTROCYTIN or MALIGNIN. After the 24 hours, the suspension is centrifuged and supernatant analyzed for protein. The complexed BAC-ASTROCYTIN or BAC-MALIGNIN is now resuspended in 0.05M aminoethanol-0.1M bicarbonate buffer pH 8.9 in order to block any unreacted bromine. The suspension is centrifuged and the supernatant is kept but not analyzed because of the presence of aminoethanol. Removal of all unbound ASTROCYTIN or MALIGNIN is then accomplished by centrifugation end resuspension for three washings in 0.15M NaCl until no absorbance is measured on the spectrophotometer at 266 m$\mu$. The BAC-ASTROCYTIN or BAC-MALIGNIN complex is now stirred in 8M urea for 2 hours at 38° C., centrifuged, then washed (three times usually suffices) with 8M urea until no absorbance is shown in the washings at 266 m$\mu$. The complex is then washed with C.15M NaCl two times to rid of urea. The complex is then stirred at 37° C. in 0.25M acetic acid for 2 hours to demonstrate its stability. Centrifuge and read supernatant at 266 m$\mu$—no absorbance should be present. This chemically complexed BAC-ASTROCYTIN or BAC-MALIGNIN is therefore stable and can now be used as a reagent in the methods described below; in this stable reagent form it is referred to as TARGET (TOPOGRAPHIC-ANTIGEN-LIKE-REAGENT-TEMPLATE) because it is a synthetically produced complex whose physical and chemical properties mimic the stable cell-bound precursor of ASTROCYTIN or MALIGNIN when it is in a potential reactive state with serum components. For storing, TARGET reagent is centrifuged and washed until neutralized with 0.15M $NaH_2PO_4$ buffer pH 7.2.

TARGET reagents may be prepared from bromoacetyl liganded carriers other than cellulose, such as bromoacetylated resins or even filter paper.

EXAMPLE 9

Production of antisera to Astrocytin, Malignin and TARGET.

Antisera to Astrocytin, Malignin or TARGET reagents may be produced by inducing an antibody response in a mammal to them. The following procedure has been found to be satisfactory.

One mg. of RECOGNIN (Astrocytin or Malignin) is injected into the toe pads of white male rabbits with standard Freund's adjuvant, and then the same injection is made intraperitoneally one week later, again intraperitoneally ten days and, if necessary, three weeks later. Specific antibodies may be detected in the blood serum of these rabbits as early as one week to ten days after the first injection. The same procedure is followed for TARGET antigen by injecting that amount of TARGET which contains 1 mg. of Astrocytin or Malignin as determined by Folin-Lowry determination of protein.

The specific antibody to Astrocytin is named Anti-Astrocytin. The specific antibody to Malignin is named Anti-Malignin. Similarly, the specific antibody to TARGET reagent is named Anti-Target.

These antibodies show clearly on standard Ouchterlony gel diffusion tests for antigen-antibody reactions with specific single sharp reaction lines produced with their specific antigen.

The presence of specific antibodies in serum can also be tested by the standard quantitative precipitin test for antigen-antibody reactions. Good quantitative precipitin curves are obtained and the micrograms of specific antibody can be calculated therefrom.

Further evidence of the presence of specific antibodies in serum can be obtained by absorption of the specific antibody Anti-Astrocytin onto Bromoacetyl-cellulose-Astrocytin (BAC-Astrocytin) prepared above. The antiserum containing specific Anti-Astrocytin can be reacted with BAC-Astrocytin. When the serum is passed over BAC-Astrocytin only the specific antibodies to Astrocytin bind to their specific antigen Astrocytin. Since Astrocytin is covalently bound to Bromoacetyl-cellulose the specific anti-body, Anti- Astrocytin, is now bound to BAC-Astrocytin to produce BAC-Astrocytin-Anti-Astrocytin (BACA-Anti-Astrocytin). This is proved by testing the remainder of the serum which is washed free from BAC-Astrocytin. On standard Ouchterlony diffusion no antibodies new remain in the serum which will react with Astrocytin. It is therefore concluded that all specific antibodies (Anti-Astrocytin) previously shown to be present in the serum, have been absorbed to BAC-Astrocytin. Furthermore, when Anti-Astrocytin is released from its binding to BAC-Astrocytin it is thereby isolated free of all contaminating antibodies. This release of Anti-Astrocytin may be accomplished by washing the BACA-Anti-Astrocytin compled with 0.25M acetic acid (4° C., 2 hrs.) which has been shown above not to break the BAC-Astrocytin bond.

Still further evidence of the presence of specific antibodies in serum can be obtained by adsorption of the specific antibody Anti-Malignin onto Bromoacetyl-cellulose-Malignin (BAC-Malignin) prepared above. The antiserum containing specific Anti-Malignin can be reacted with BAC-Malignin. When the serum is passed over BAC-Malignin only the specific antibodies to Malignin bind to their specific antigen Malignin. Since Malignin is covalently bound to Bromoacetyl-cellulose the specific antibody, Anti-Malignin, is now bound to BAC-Malignin to produce BAC-Malignin-Anti-Malignin (BACM-Anti-Malignin). This is proved by testing the remainder of the serum which is washed free from BAC-Malignin. On standard Ouchterlony diffusion no antibodies now remain in the serum which will react with Malignin. It is therefore concluded that all specific antibodies (Anti-Malignin) previously shown to be present in the serum, have been absorbed to BAC-Malignin. Furthermore, when Anti-Malignin is released from its binding to BAC-Malignin it is thereby isolated free of all contaminating antibodies. This release of Anti-Malignin may be accomplished by washing the BACM-Anti-Malignin complex with 0.25M acetic acid (4° C., 2 hrs.) which has been shown above not to break the BAC-Malignin bond.

The antibodies to TARGET show clearly on standard Ouchterlony gel diffusion tests for antigen-antibody reactions with specific single reaction lines produced with TARGET which show a line of identity with the line of reaction to ANTI-ASTROCYTIN or ANTI-MALIGNIN antisera (i.e., that produced to the injection of ASTROCYTIN or MALIGNIN themselves). Some rabbits, it has been noted, have levels of ANTI-TARGET in their blood prior to being injected with TARGET. These ANTI-TARGET substances, when reacted specifically With TARGET reagent as to be described in tests of human sera, lead to the production of approximately equivalent amounts of the two types of TAG, S-TAG; and F-TAG (see later EXAMPLES).

EXAMPLE 10

Detection of Malignant Tumors by Quantitative Production in vitro of TARGET-ATTACHING-GLOBULINS (TAG) from Biological Fluids.

TARGET reagent prepared in accordance with EXAMPLE 8 is washed to remove any unbound RECOGNIN which may be present due to deterioration. The following procedure is satisfactory. TARGET reagent is stirred for two hours at 37° C. with acetic acid, centrifuged, the supernatant decanted, and the optical density of the supernatant read at 266 m$\mu$. If there is any absorbance, this wash is repeated until no further material is solubilized. The TARGET is then resuspended in phosphate buffered saline, pH 7.2. (Standard S-TAG and F-TAG purified from previous reactions of human serum by the procedure described below can be used if available, as reference standards to test the TARGET reagent, as can whole rabbit serum which has been determined to contain S-TAG and F-TAG by other TARGET preparations).

The Slow-Binding (S-TAG) determination is performed as follows: Frozen serum stored more than a few days should not be used. Serum is carefully prepared from freshly obtained whole blood or other body fluid by standard procedures in the art. The following procedure has been found to be satisfactory. Blood is allowed to clot by standing for 2 hours at room temperature in a glass test tube. The clots are separated from the walls with a glass stirring rod, and the blood allowed to stand at 4° C. for a minimum of 2 hours (or overnight). The clots are separated from the serum by centrifuging at 20,000 rpm at 4° C. for 45 minutes. The serum is decanted into a centrifuge tube and centrifuged again at 2000 rpm at 4° C. for 45 minutes. The serum is decanted and a 1% Solution of Methiolate (1 g. in 95 ml. water and 5 ml. 0.2M bicarbonate buffer pH 10) is added to the extent of 1% of the volume of serum.

Serum samples, prepared by the above or other procedures, of 0.2 ml each are added to each of 0.20 ml aliquots of TARGET suspension reagent containing 100–200 micrograms of RECOGNIN per 0.20 ml. TARGET reagent, in duplicate determination. The suspension is mixed at 4° C. in a manner to avoid pellet formation. For example, a small rubber cap rapid shaken may be used for 1–2 seconds and then, with the tubes slightly slanted, they may be shaken in a Thomas shaker for about 2 hours or more. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2–0.3 ml. of 0.15M Saline, centrifuged and the supernatants discarded.

The protein which remains attached to the TARGET is cleaved therefrom and quantitatively determined. For example, 0.2 ml. of 0.25M acetic acid is added, the suspension shaken for 1 to 2 seconds with a rubber cap shaker, then in a Thomas shaker for about 2 hours in a 37° C. incubator. The tubes are centrifuged at 2000 rpm at 4° C. for 30 minutes. The supernatant is carefully decanted to avoid transfering particles and the optical density of the supernatant is read at 280 m$\mu$. The value of the optical density is divided by a factor of 1.46 for results in micrograms per ml. serum protein (S-TAG). Duplicate determinations should not very more than 5%. Any other procedure effective for determining protein content may be used, such as Folin-Lowry determination, but standards must be specified to determine the range of control and tumor values of S-TAG and F-TAG concentration.

The Fast-Binding (F-TAG) determination is performed as follows: Frozen serum stored more than a few days should not be used. Serum is carefully prepared from freshly obtained whole blood or other body fluid by standard procedures in the art. The procedure given above in this EXAMPLE for serum preparation is satisfactory.

Serum samples, prepared by the above or other procedures are allowed to stand at 4° C. for 10 minutes less than the total time the S-TAG serum determinations were allowed to be in contact with TARGET reagent above (e.g., 1 hour 50 minutes if a "two hour" S-TAG determination was made). This procedure equilibrates the temperature histories of S-TAG and F-TAG determinations.

Add 0.2 ml. samples of the temperature equilibrated serum to each of 0.20 ml. aliquots of TARGET suspension reagent containing 100–200 micrograms of RECOGNIN per 0.20 ml. TARGET reagent, in duplicate determination. The suspension is then mixed at 4° C. for approximately 10 minutes in a manner to avoid pellet formation. For example, a small rubber cap rapid shaker may be used for 1–2 seconds and then, with the tubes slightly slanted, they may be shaken in a Thomas shaker for approximately 10 minutes. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2–0.3 ml. of 0.15M Saline, centrifuged and the supernatants discarded.

The protein which remains attached to the TARGET is cleaved therefrom and quantitatively determined. The procedure described above in this EXAMPLE for determining S-TAG concentration is satisfactory. Any other procedure effective for determining protein content may be used, such as Folin-Lowry determination, but standards must be specified to determine the range of control and tumor values of S-TAG minus F-TAG concentration.

The final results are expressed as TAG micrograms per ml. of Serum, and equal S-TAG minus F-TAG. TAG values in non-brain-tumor patients and other controls currently range from zero (or a negative number) to 140 micrograms per ml. of serum. TAG values in the first patients studied, brain tumor patients, ranged from 141 to 500 micrograms per ml. of serum. In the first "blind" study of 50 blood samples conducted according to the procedures of this EXAMPLE utilizing TARGET reagent prepared from Astrocytin and bromoacetylcellulose, 11 of 11 brain tumors and 28 of 32 normals were correctly identified. One of the 4 supposed normals (i.e., non-brain tumor controls) turned out to have a cancer of the thyroid gland which had apparently been successfully treated some years before. The three remaining normals were individuals aged 60–70 who were in poor health, possibly having nondiagnosed cancer. Of the remaining 7 samples, three out of three cases of Hodgkin's Disease were correctly identified; one sample in the tumor range (141–500 $\mu$g. TAG/ml.) corresponded to patients having respectively, an intracranial mass diagnosis uncertain but non-tumor, and osteosarcoma (non-brain tumor) and a melanotic sarcoma (non-brain tumor).

Subsequent blind studies conducted according to the procedures of this example utilizing TARGET reagent prepared from MALIGNIN and bromoacetylcellulose correctly identified three out of three malignant brain tumors and all normals, then were continued as detailed in EXAMPLE 10A which follows.

EXAMPLE 10A

Determination of Anti-Malignin Antibody in 1,026 Cancer Patients and Controls: A Seven-Year Nine Hospital Blind Study.

The antibody to malignin, a cancer cell 10,000 Dalton polypeptide of known composition, was quantitatively determined blind by specific immuno-adsorption in 1,094 serum specimens from 1,026 cancer patients and controls. Anti-malignin antibody, known to be cytotoxic to cancer cells in vitro, was elevated in 92.7% of sera from patients with clinically and pathologically active cancer (mean 273.7±156.5 micrograms/ml) compared with healthy normal subjects (mean 59.1±27.0 micrograms/ml) in a broad range of types of malignancy in support of the hypothesis that malignin is a general transformation antigen. The antibody was in the normal range (0–134 micrograms/ml) in 100% of sera of healthy normal subjects (first control group), in 94.6% of sera of out-patient hospital non-cancer controls (mean 64.3±46.3 micrograms/ml) (second control group) and in 91.2% of sera of in-patient medical-surgical disorder non-cancer patients (mean 81.2±67.3 micrograms/ml) (third control group). That only an active cancer state appears to be associated with elevated antibody levels is supported by the finding that the antibody was in the normal range in 94.2% of sera from cancer patients who had been successfully treated and clinico-pathologically showed 'no evidence of disease' at the time of the determination (fourth control group) (mean 70.1±36.7 micrograms/ml). None of the four control groups was statistically significantly different from each other, but each control group differed from the active cancer group at a level of P<0.000001. Of the 109 cancer patients who had antibody levels below 135 micrograms/ml, 90 (83.3%) were dead within one year (mean 4.4±3.5 months). Of the 76 active cancer patients who could be followed and who were still alive beyond one year and up to 46 months (mean 22.0±8 months) after the antibody determination, 68 (89.5%) had had antibody levels above 135 micrograms/ml. The relationship of the concentration of anti-malignin antibody to survival suggested by these data as well as some diagnostic and therapeutic implications are noted.

A general transformation antigen is one which is common to the process of malignant transformation rather than to the particular cell type involved. The general antigen therefore differs from cell-specific tumor markers which are related to the products of the particular type of cell transformed, as in the case of insulin or thyroid hormone excesses produced by pancreatic or thyroid neoplasms respectively (7). Malignin, a 10,000 dalton polypeptide from malignant glial cells, with a high content of glutamic acid and aspartic acid and a high ratio of these two amino acids to histidine, reported in 1975 (1–3), and its close structural relatives astrocytin, recognin lymphoma) and recognin M (mammary carcinoma) 2,4) are members of what appears to be the first chemically and immunologically defined family of general transformation antigens. These antigens, or anti-malignin antibody which reacts with each, have been determined in the cells and sera of patients with a variety of neoplasms, in induced malignant transformations in animals and in the cells and supernates of malignant cells growing in tissue culture (5–7,12). Other transformation antigens, not quite as general but broad in representation, are new being identified in other laboratories in experimental cell transformations induced by chemical and viral means (8,9).

Over the past seven years we have examined the possible relation of malignin and anti-malignin antibody to human cancer states. Previous tumor-associated antigens studied in humans, such as the carcinoembryonic antigens (10) have exhibited varying demonstrability in different types of cancer and low concordance with clinical diagnoses. Perhaps due to the fact that none have had constant chemically defined composition or mode of production, the inconstantly released mixtures of antigens rather than a potentially more constant level of specific antibody have had to be measured in serum. Malignin is produced in constant tissue culture of malignant cells, is of known and reproducible composition, and its antibody has been demonstrated to be present in and isolated from the serum of patients with cancer (6,7). The antibody and antigen studies reported here support the apparently ubiquitous distribution of the malignin antigen or its very close structural relatives in active cancer of all types examined.

METHODS

Patients and Controls a) Serum Anti-Malignin Antibody Studies

Cancer patients were chosen by the clinical investigators at each of nine hospitals from various types of cancer in the approximate frequency of their rate of occurrence in their population or of the investigator's particular interest (see Table 1). Untreated as well as treated cases were accepted. Of the resultant 500 cancer sera studied, 247 (49.4%) were from patients who had clinically and pathologically defined and successfully treated cancer up to 15 years earlier and had no clinical or pathological evidence of disease at the time the antibody was determined (fourth control group, below). Of the active cancer group, 76 patients could be followed who were still alive beyond one year and up to 46 months. Four control groups were studied: (1) 59 healthy normals (60 sera); (2) 56 hospital out-patients with some symptoms but without definite clinical diagnosis (56 sera);(3) 258 hospital in-patients with definite medical-surgical diagnoses (261 sera); and (4) the 86 cancer patients referred to above who had no evidence of disease at the time of the determination. The medical-surgical diagnoses in the third control group included bacterial infections (26 sera), viral infections (28 sera), trauma (8 sera), cardiovascular disorders (30 sera), gastrointestinal and hematopoietic disorders (39 sera), thoracic disorders (6 sera), obstetrical and gynecological disorders (7 sera), genitourinary disorders (11 sera), endocrine metabolic and arthritic disorders (22 sera), neurologic disorders (62 sera), psychiatric disorders (6 sera), and skin disorders (16 sera). In addition to the above randomly collected sera, selective blind studies have been initiated but not completed on several specific groups: 45 patients with multiple sclerosis (49 sera) and 57 with benign tumors (74 sera), as well as on 31 blood relatives ('relatives') of cancer patients (31 sera), on people in contact with canter patients, that is, 54 non-blood relatives and hospital staff ('contacts') (63 sera). 84% of the sera came from the Medical College of Ohio at Toledo.

b) Immunochemical Methods

Serum anti-malignin antibody was quantitatively determined by an immunoabsorption method previously described in which the serum antibody is specifically adsorbed to immobilized malignin ('Target' reagent) in a 2-hour (slow) and a 10-minute (fast) reaction, then released in soluble form and read by optical density at 280 millimicrons as micrograms of antibody protein (11). The values of anti-malignin antibody are expressed as net Target-attaching-globulins ('Net-TAG') calculated: 2-Hour immunoadsorption Slow (S) TAG less the 10-Minute immunoadsorption Fast (F) TAG. All values given represent Net TAG unless otherwise noted. The Net TAG does not appropriately reflect the antibody elevation when the F-TAG is markedly elevated to between 270 and 1100 micrograms/ml. In these instances, seen rarely in the four control groups (2 of 464 sera, 0.4%), but in 58 on 247 active cancer sera (23.5%), the S-TAG values are also elevated to above 400 and as much as 12,00 micrograms/ml. In the accompanying figures, to distinguish these cases of extraordinary increase in both forms of antibody, rather than adding the values for the two forms, only the S-TAG has been plotted as open circles. These cases have been examined statistically in two ways, separately, and as part of the clinically determined active cancer group. The antibody determinations were performed blind on coded specimens of sera by laboratory personnel who were in a different center than the one in which the specimens were collected.

c) Correlation of Clinical and Laboratory Data

Correlations were made for each patient after completion and recording of both clinical and laboratory data separately. The error for these correlations in terminal cases is likely to be very small since it involved pathologically confirmed cancer and two reliable dates: the date of the antibody determination and the date of death. For each of 206 of the 247 active cancer cases, in addition to the absence of their names from the tumor registry of deaths, it was possible to verify by contacting each patient or their physician that the patient was still alive at the end of one year. For 41 of these cases, the contact verification either was not possible or possible only to the tenth month. Since most of these 41 cases were from the first two years of the study) when clinically terminal patients were actively excluded from the study, this is not likely to represent an appreciable error. At most, the number in the active cancer group would be reduced and the number in the terminal group increased, each by 41, neither of which would significantly influence the conclusions reached except for the value of the mean for the antibody in the terminal group which would be increased. In the statistical comparison of the groups, values of P 0.01 were considered statistically significant. The only comparison of those found not significant under these criteria which approached but did not quite reach the 0.05 level was between the first two control groups (FIG. 1).

RESULTS

FIG. 1 shows the concentration of anti-malignin antibody, in micrograms/ml, serum in individual sera, in the four control groups and the active cancer group: that is) 1) healthy normals, 2) cancer patients showing no evidence of disease after successful treatment, 3) out-patients (non-cancer) with medical-surgical symptoms but without defined disorders, 4) in-patients (non-cancer) with defined medical-surgical disorders, and 5) patients with active cancer who lived one year or longer. While the four control groups did not differ from each other at a statistically significant level, each differed from the active cancer group at the significant level of P 0.000001.

Figure 2B:
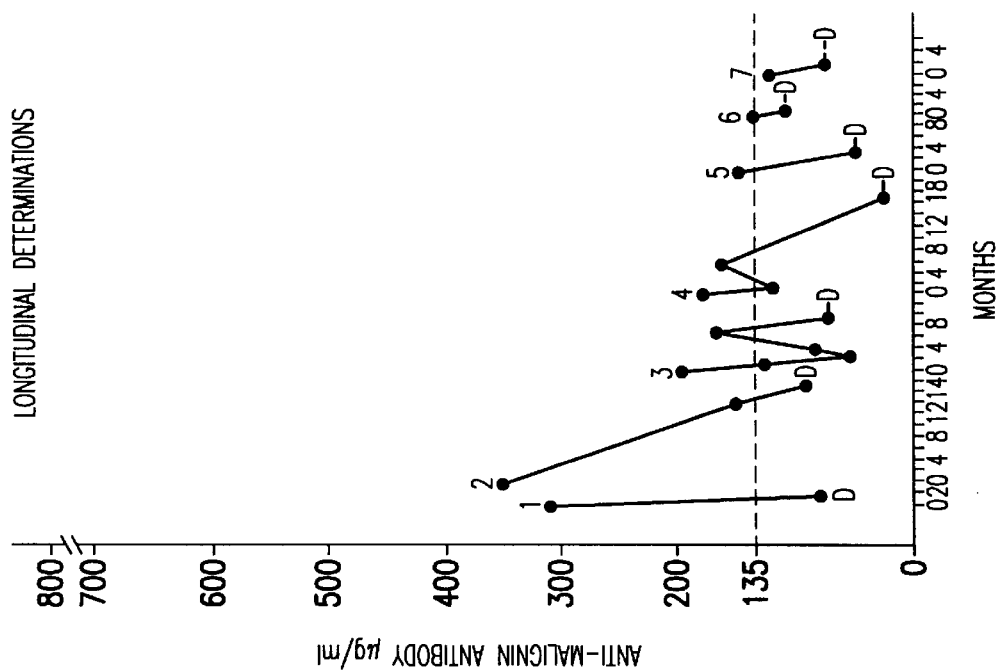
FIG. 2B is a graph of the concentration of anti-malignin antibody in patients' sera over time (months).
Figure 2A:
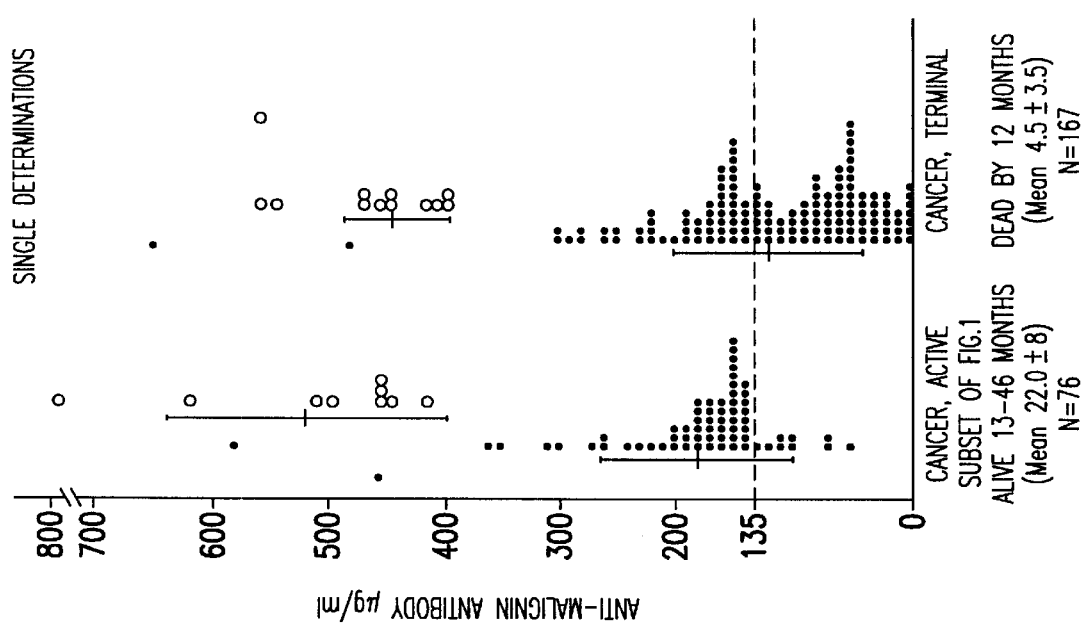
FIG. 2A is a plot of the concentration of anti-malignin antibody in sera of individual patients with terminal cancer.

FIG. 2A shows the concentration of anti-malignin antibody in individual sera of patients with terminal cancer, that is, those who died within one year (mean 4.4±3.5 months). The concentration of antibody in this group differs statistically from the active cancer group at a level of <4 0.000001. Together with the data shown in FIG. 1, it may be seen that 90 of 108 cancer patients (83.3%) who had antibody levels below 135 micrograms/ml died within one year. In contrast, of the 76 active cancer patients who ware longer term survivors and who could be followed 13 to 46 months (Lean 22.3±8) after the antibody determination, 68 (89.5%) had had elevated antibody levels. FIG. 2B shows seven examples of the decrease before death observed in individual patient's serum anti-malignin antibody levels when determined serially.

Table 1 shows the types of cancer patient studied, and the distribution of samples between active disease, terminal disease and no evidence of disease in each type of cancer. The distribution of type of cancer is fairly typical with the exception of an excess number of brain cancer cases which was the initial focus of interest of the study.

In the beginning blind study in each of the non-random preselected groups the antibody level was elevated in the sera of 20.4% of patients with multiple sclerosis, 31.1% of patients with benign tumors, 30.2% of 'contacts' of active cancer patients and 38.7% of blood relatives of active cancer patients.

EXAMPLE 10A

TABLE I

DISTRIBUTION OF NUMBER OF SERUM ANTI-MALIGNIN ANTIBODY DETERMINATION ACCORDING TO TYPE OF MALIGNANCY AND CLINICAL STATUS

| TYPE OF MALIGNANCY | TOTAL NUMBER | CLINICAL STATUS | | |
|---|---|---|---|---|
| | | Active Disease | No Evidence Disease | Terminal |
| Carcinoma of: | | | | |
| Lung | 38 | 11 | 1 | 26 |
| Larynx | 3 | 2 | 1 | |
| Breast | 67 | 26 | 27 | |
| Uterus | 5 | 1 | 1 | 3 |
| Cervix | 6 | 3 | | 3 |
| Ovary | 11 | 3 | 3 | 5 |
| Vulva | 1 | | | 1 |
| Colon | 37 | 18 | 3 | 16 |
| Rectum | 13 | 9 | 2 | 2 |
| Stomach | 2 | 1 | | 1 |
| Oesophagus | 3 | 1 | | 2 |
| Bile Duct | 1 | | | 1 |
| Prostate | 13 | 7 | 4 | 2 |
| Bladder | 12 | 5 | 4 | 3 |
| Urethra | 1 | 1 | | |
| Kidney | 15 | 6 | 5 | 4 |
| Testis | 7 | 1 | 5 | 1 |
| Thyroid | 4 | 4 | | |
| Pancreas | 4 | | | 4 |
| Adrenal | 1 | | | 1 |
| Skin | 5 | 1 | 3 | 1 |
| Undifferentiated | 14 | 9 | | 5 |
| Hodgkins' Disease | 14 | 8 | 3 | 3 |
| Lymphoma | 25 | 15 | 9 | 1 |
| Multiple Myeloma | 15 | 10 | 2 | 3 |
| Acute Myelogenous Leukemia | 3 | 2 | | 1 |
| Acute Lymphocytic Leukemia | 1 | | 1 | |
| Chronic Myelogenous Leukemia | 8 | 7 | | 1 |
| Chronic Lymphocytic Leukemia | 8 | 4 | 2 | 2 |
| Fibrosarcoma | 1 | 1 | | |
| Melanotic Sarcoma | 15 | 8 | 4 | 1 |
| Osteogenic Sarcoma | 6 | 1 | 1 | 4 |
| Rhebdomyosarcoma | 4 | | 1 | 3 |
| Liposarcoma | 1 | 1 | | |
| Hemangioblastoma | 1 | 1 | | |
| Histiocytoma | 1 | | | 1 |
| Brain Cancer | 133 | 80 | 2 | 51 |
| Retinoblastoma | 1 | | 1 | |
| | 500 | 247 | 86 | 167 |

Legend for FIG. 1
EXAMPLE 10A

Concentration of anti-malignin antibody in four control groups and in active cancer patients. Solid circles, Net TAG; open circles, S-TAG (F-TAG excess). See Methods for details.

Legend for FIG. 2
EXAMPLE 10A

Relation of level of anti-malignin antibody to terminal clinical state. Solid circles, Net TAG; Open circles, S-TAG (F-TAG excess). See Methods for details.

A. Single blind determination in individual patients.

B. Longitudinal blind determinations on seven individual cancer patients (1 through 7) whose death (D) occurred 1 to 4 months from date last specimen determined.

DISCUSSION

The data obtained in this blind study are consistent with the previous evidence that malignin is a general transformation antigen. Thus rather than being restricted to particular cell types, anti-malignin antibody was elevated significantly above normal levels, and malignin was visualized in cells, in patients with a broad variety of active cancer (Table 1 and Methods b.) That the antibody was in the normal range in 94.2% of patients who had been successfully treated and at the time of the antibody determination showed no evidence of disease, suggests that an active cancer state is required to maintain elevated antibody levels. In the separation of healthy normal subjects from active cancer patients by determination of anti-malignin antibody, all healthy normals had values below 135 (mean 59.1±27.0) micrograms/ml and there were no 'false positives', while in the active cancer group, 92.7% showed elevated values of antibody (mean 273.7±156.5 micrograms/ml). The healthy normal and the active cancer groups differed at a level of $P<0.000001$ for the whole active cancer group, as well as for each of the two subgroups shown in FIG. 1.

As medically-ill subjects are brought into the comparison (FIG. 1) the mean levels of concentration of antibody are seen to shift slightly but no significantly upward. In the out-patient non-cancer group, 94.6% were still in the normal range, and 5.4% were in the elevated range. In the in-patient, more clearly ill, positively diagnosed (but apparently non-cancer) medical-surgical group, 91.2% were still in the normal range, and 8.8% were in the elevated range. These two control groups were not statistically significantly different from the healthy normal control group but each differed from the active cancer group at a level of P<0.000001. It might be expected that compared with healthy normals, the incidence of cancer would be greater in medically ill patients and that some of these cancer cases might not yet be clinically diagnosable. How many of these presumptive 'false positives' actually represent occult cancer not yet clinically detected cannot be predicted, but it is relevant to note that six additional 'false positives' were found from one to 19 months later actually to have clinically and pathologically proven cancer.

The data in the preselected groups, although blind, were not randomly collected as were those in FIGS. 1 and 2 and therefore cannot be pooled with them. Each of these preselected groups is considered too small to form conclusions because of heterogeneity of each and the complexity of the implications raised by the data, but they are included as preliminary data for the sake of completeness. There is a possibility that in the destructive and immune reactions in the nervous system in multiple sclerosis that a higher false positive rate may occur. Some of this may represent misdiagnosed central nervous system malignancy. Sera from patients with benign tumors might be expected to show a higher false positive rate consistent with the borderline area in clinico-pathological diagnosis between benign and malignant growths. Anti-malignin antibody levels and the demonstration of malignin in cells may in the future help to clarify the definition in this group. The observation of a higher incidence of elevated anti-malignin antibody in contacts of active cancer patients. (compared with healthy normals P<0.001) is in agreement with several previously published studies on other tumor indexes demonstrating the same curious phenomenon (14 clinical studies and one laboratory study cited in reference 14). Whether this represents some form of immunization against a transmittable agent, either the malignin antigen itself or a substance which induces transformation and thus the appearance of the antigen, needs more work to clarify. Finally, the greatest incidence of antibody elevation in a 'non-cancer' group is observed in the blood relatives of active cancer patients. Whether this represents a response to actual cell transformation, a genetically determined high level of production of the antibody for immunosurveillance, or the same phenomenon as that observed in the 'contacts' group is unknown. Since the 'relatives' are statistically different from the 'healthy normal' control group at a level of P<0.000001, some explanation will have to be sought and certainly much larger groups will have to be examined.

The utility of the malignin antigen and the antibody for general screening of populations for cancer is suggested by the low 'false positive' rates shown in FIG. 1 in the healthy normal and out-patient control groups. The results of the present studies also indicate, within the limitations of all laboratory procedures, that both the determination in cells of malignin and in serum of its antibody may be useful in helping to recognize the presence of malignant states in individuals in whom cancer is suspected. In addition, the clinical follow-up of individual patients over months and years has permitted the comparison of clinical outcome with antibody levels which were obtained on blind coded serum specimens. The correlation observed suggests that the anti-malignin antibody level may be related to survival in that the elevated values during active disease were associated with longer survival and low levels during active disease with early death. After successful treatment, however, the presence of normal (low) antibody levels may be an aid in determining whether an active cancer state has been replaced by one in which there is 'evidence of disease'. Once again, the laboratory value can have relevance only in relation to the clinical status, and it usually should not be difficult to separate the clinically healthy from the clinically terminal patient, both of whom have low levels of antibody, but for different reasons.

The significance of the correlation of lower levels of anti-malignin antibody with terminal illness shown in FIG. 2A and 2B is not known. Since as seen in FIG. 23, the drop in antibody can occur abruptly, in as little as one month before death, it is not known how many of the elevated values shown in FIG. 2A were followed by a similar drop prior to death. The drop may therefore be even more common then observed in the single determinations. The phenomenon is in accord with previous demonstrations by others of the general decrease in immunocompetence observed to signal oncoming death in both human and animal cancer (15), and may simply represent a secondary consequence of the terminal state. However, since anti-malignin antibody is specific for a cancer cell antigen, localized preferentially in malignant cells in vitro and in vivo, and has been shown to be cytotoxic to malignant cells in vitro (7), the drop in antibody might be more central to the cancer process and be to the detriment of the patient. In addition, earlier data (6) showed anti-malignin antibody in human cancer sera to be largely 'disarmed', with its Fc portion cleaved from the Fab fragments, which would result in loss of cytotoxicity. This process might reflect one form of the cancer cell's defense against the antibody. The low levels of antibody observed here prior to death may be evidence of a second form of the cancer cell's defense, the result of increasing blockade of antibody production or release due to antigen excess as the tumor proliferates.

That malignin is not an 'onco-fetal' antigen is supported by the absence of malignin from fetal tissues. Malignin appears to be much older phylogenetically than those states commonly thought of as being recapitulated during fetal development; its only structural relatives, by computer search (16), are the ferredoxins of plants, lucaena glauca and alfalfa, the acyl carrier protein of *E. coli*, and cytochrome b5. These four share the property of being anaerobic enzymes, the ferredoxins being the most electro-negative oxidation-reduction enzymes in nature. Warburg observed the anaerobic advantage of malignant cells but was unable to account for this property in the activity of the then known anaerobic enzymes (17). The possibility that malignin is a cleaved derivative of such an anaerobic enzyme system, that this system is common to all malignancies regardless of cell type, and that this system imparts a unique anaerobic advantage to canner cells, would be consistent with the demonstrated increase in the yield or malignin with increasing malignancy of cell growth (1,2), the ubiquity of distribution of the antigen, the cytotoxicity of the antibody and the antibody failure in the terminal state. Now that purified human anti-malignin antibody is available (6,7), and monoclonal anti-malignin antibodies are available, the therapeutic uses of the antibody acting alone or as a carrier for anti-cancer drugs can be further systematically examined.

REFERENCES FOR EXAMPLE 10A

1. Bogoch, S. Brain glycoproteins and recognition function: Recognins and cancer. Pages 555–556. In Volk, B. W. and Schneck, L. (eds), *Current Trends in Sphingolipidoses and Allied Disorders*, Plenum Press, New York, 1976.
2. Bogoch, S. Astrocytin and malignin: Two polypeptide fragments (recognins) related to brain tumor. *Nat. Cancer Inst. Mon.* 46: 133–137, 1977.
3. Bogoch, S. The detection of malignant gliomas in brain by the quantitative production in vitro of TAG (target-attaching globulins) from human serum. Pp. 358–361. In Bogoch, S. (ed) *Biological Diagnosis of Brain Disorders*. Spectrum-Wiley Press, New York) 1974.
4. Bogoch, S. and Bogoch, E. S. Production of two recognins related to malignin: Recognin M from mammary MCF-7 carcinoma cells and recognin L from $P_3J$ lymphoma cells. *Neurochemical Res.* 4: 465–472, 1979.
5. Bogoch, S., Bogoch, E. S., Fager, C., Goldensohn, E., Harris, J. H., Hickok, D. F., Lowden, J. A., Lux, W. E., Ransohoff, J., and Walker, M. D. Elevated anti-malignin antibody in the serum of cancer patients: A multi-hospital blind study. *Neurology* 29: 584, 1979.
6. Bogoch, S., and Bogoch, E. S. Disarmed anti-malignin antibody in human cancers *Lancet*, 1, 987, 1979.
7. Bogoch, S. and Bogoch, E. S. Tumor markers: Malignin and related recognins associated with malignancy rather than with cell type. In Battistin, L., Hashim, G., and Lajtha, A. (eds) *Neurochemistry and Clinical Neurology*, pp. 407–424. Alan R. Liss, Inc., New York, 1950.
8. Rigby, P. The transforming genes of SV40 and polyoma viruses. *Nature* 282: 781–784, 1979.
9. Langan, T. Malignant transformation and protein phosphorylation. *Nature* 286: 329–330, 1980.
10. Krupey, J., Gold, P. and Freedman, S. O. Physicochemical studies of the carcinoembryonic antigens of the human digestive system. *J. Exptl. Med.* 128: 387–395, 1968.
11. Bogoch, S. and Bogoch, E. S. Quantitative determination of anti-malignin antibody. In Rosenberg, S. A. (ed) *Serologic Analysis of Human-Cancer Antigens*, pp. 693–696. Academic Press, Inc., New York, 1980.
12. Harris, J. H., Gohara, A., Redmond, F., Bogoch, S. and Bogoch, E. S. Immunofluorescent and serologic studies with anti-malignin antibody. In Rosenberg S. A. (ed) *Serologic Analysis of Human Cancer Antigens*, pp. 571–582. Academic Press, Inc., New York, 1980.
13. Meck, R. A., Ingram, M., Meck, J. J., McCullough, J. L., Wu, M-C, and Yunis, A. A. Establishment and Cell Cycle Kinetics of a Human Squamous Cell Carcinoma in Nude Mice and in Vitro. *Cancer Res.* 4: 1076–1085, 1981.
14. Editorial, The Cancer Connection. *Lancet* 1: 635–636, 1977.
15. Hersh, E. M., Gutterman, J. U., Mavligit, G. M., Mountain, C. W., McBride, C. M., Burgess, M. A., Lurie, P. M., Zelen, M., Takita, H. and Vincent, R. G. Immunocompetence, Immunodeficiency and Prognosis in Cancer. *Ann. New York Acad. Sci.* 276: 386–406, 1976.
16. Dayhoff, M. O. (ed) *Atlas of Protein Sequence and Structure*. National Biomedical Research Foundation, Silver Springs, Md., 1972.
17. Warburg, O., Gaweh, K., Geissler, A. W., Schroder, W., Gewitz, H. S. and Volker, W. *Arch. Biochem. Biophys.* 78: 573, 1958.

EXAMPLE 10B

Serum samples were obtained from 354 individuals from 4 oncologists (located in New York, Ohio and Rhode Island) along with clinical histories and/or histo-pathological data. 211 Of the samples were obtained from individuals who did not have cancer.

The serum in each sample was separated from the clot within 1 hour after venipuncture. Each sample was then frozen and shipped in dry ice to a central laboratory for testing. Analyses were performed within 72 hours of clotting and serum separation. The samples were coded and the results were not matched with clinical histories or diagnoses until after the analyses had been completed.

In the analyses, anti-malignin antibody was quantified by the immunoabsorption method of Example 10A.

Survival was analyzed by the actuarial or life-table method wherein the surviving fraction is calculated as a function of time. This method was applied month by month for 12 months in the study of Example 10B.

RESULTS

Table II shows the distribution of cancer types for those 143 cancer patients included among the 354 individuals from whom samples were drawn.

TABLE II

NUMBER OF SERUM ANTI-MALIGNIN ANTIBODY DETERMINATIONS ACCORDING TO TYPE OF MALIGNANCY AND CLINICAL STATUS

| TYPE/LOCATION OF MALIGNANCY | TOTAL NUMBER | % | ACTIVE DISEASES | NO CURRENT EVIDENCE OF DISEASES | TERMINAL | UNKNOWN OUTCOME |
|---|---|---|---|---|---|---|
| Lung | 14 | (9.8) | | | 12 | 2 |
| Larynx | 1 | (0.7) | | 1 | | |
| Breast | 20 | (14.3) | 2 | 6 | 8 | 4 |
| Uterus | 3 | (2.1) | | 1 | 2 | |
| Cervix | — | — | | | | |
| Cvary | 3 | (2.1) | 1 | | | 2 |
| Colon | 12 | (8.4) | 1 | 5 | 6 | |
| Rectum | 3 | (2.1) | | | | 3 |
| Anus | 2 | (1.4) | 1 | | 1 | |
| Stomach | 3 | (2.1) | | 1 | 2 | |
| Gall Bladder | 1 | (0.7) | | | 1 | |
| Prostate | 5 | (3.5) | | | 3 | 2 |
| Ureter | 1 | (0.7) | | | | 1 |
| Kidney | 2 | (1.4) | | | 2 | |

TABLE II-continued

NUMBER OF SERUM ANTI-MALIGNIN ANTIBODY DETERMINATIONS
ACCORDING TO TYPE OF MALIGNANCY AND CLINICAL STATUS

| TYPE/LOCATION OF MALIGNANCY | TOTAL NUMBER | % | ACTIVE DISEASES | NO CURRENT EVIDENCE OF DISEASES | TERMINAL | UNKNOWN OUTCOME |
|---|---|---|---|---|---|---|
| Testis | 2 | (1.4) | 1 | 1 | | |
| Thyroid | 1 | (0.7) | | 1 | | |
| Pancreas | 1 | (0.7) | | | 1 | |
| Umdifferentiated | 13 | (9.3) | 1 | 1 | 7 | 4 |
| Hodgkins' Disease | 5 | (3.6) | | 3 | 2 | |
| Lymphoma | 9 | (6.3) | 2 | 2 | 2 | 3 |
| Multiple Myeloma | 1 | (0.7) | | | 1 | |
| Acute Myel. Leukemia | 4 | (2.8) | 1 | 2 | 1 | |
| Acute Lymph. Leukemia | 2 | (1.4) | 1 | | 1 | |
| Ch. Myel. Leukemia | 3 | (2.1) | | | 1 | 2 |
| Ch. Lymph. Leukemia | 6 | (4.2) | 1 | 1 | 2 | 2 |
| Fibrosarcoma | 1 | (0.7) | | | | 1 |
| (Sarcoma) | 18 | (12.6) | 6 | 5 | 7 | |
| Leicmyosarcoma | 2 | (1.4) | 1 | 1 | | |
| Liposarcoma | 1 | (0.7) | | | | 1 |
| Giant Cell Sarcoma | 1 | (0.7) | | 1 | | |
| Mesothelioma | 1 | (0.7) | 1 | | | |
| Synovial cell | 1 | (0.7) | | | 1 | |
| Brain Cancer | 1 | (0.7) | | | 1 | |
| Other | — | — | | | | |
| Total | 143 | | 20 | 32 | 64 | 27 |

Table III presents a comparison of the clinical history for the individuals within both Example 10B and Example 10A with the results of the anti-malignin antibody analyses.

TABLE III

Comparison of the RESULTS FROM EXAMPLE 10B WITH THE RESULTS FROM EXAMPLE 10A

| | EXAMPLE 10B | | | EXAMPLE 10A | | |
|---|---|---|---|---|---|---|
| | N | % Normal* | % Abnormal* | N | % Norm* | % Abn* |
| Clinical Background | | | | | | |
| Healthy Normal | 101 | 94.1 | 5.9 | 60 | 100 | 0 |
| No evidence of disease (treated Ca) | 32 | 96.9 | 3.1 | 86 | 94.2 | 5.8 |
| Out Patient Med/Surg | — | — | — | 56 | 94.6 | 5.4 |
| In-Patient Med/Surg. | 110 | 93.6 | 6.4 | 261 | 91.2 | 8.8 |
| Active Cancer | 20 | 0 | 100 | 247 | 7.3 | 92.7 |
| Terminal Cancer | 1`64 | 79.7 | 20.3 | 167 | 52.1 | 47.9 |

* From Anti-Malignin antibody tests: normal: 0–134 mg/ml; abnormal (elevated): 135 mg/ml or greater Duplicate samples were run for 80 of the Example 10B samples and in 94% of the duplicate samples, the second determination agreed, i.e., the results were in the same range (normal or abnormal) with the initial determination.

All of the samples from patients whose clinical history showed an active cancer also had an elevated level of anti-malignin antibodies. The mean anti-malignin antibody concentration among those patients with an active cancer was 186 u g/ml. In contrast, only 3 to 6 percent of the individuals, who according to their clinical history, did not have cancer had elevated anti-malignin antibody levels. This false-positive rate confirms the data of Example 10A.

Figure 3:
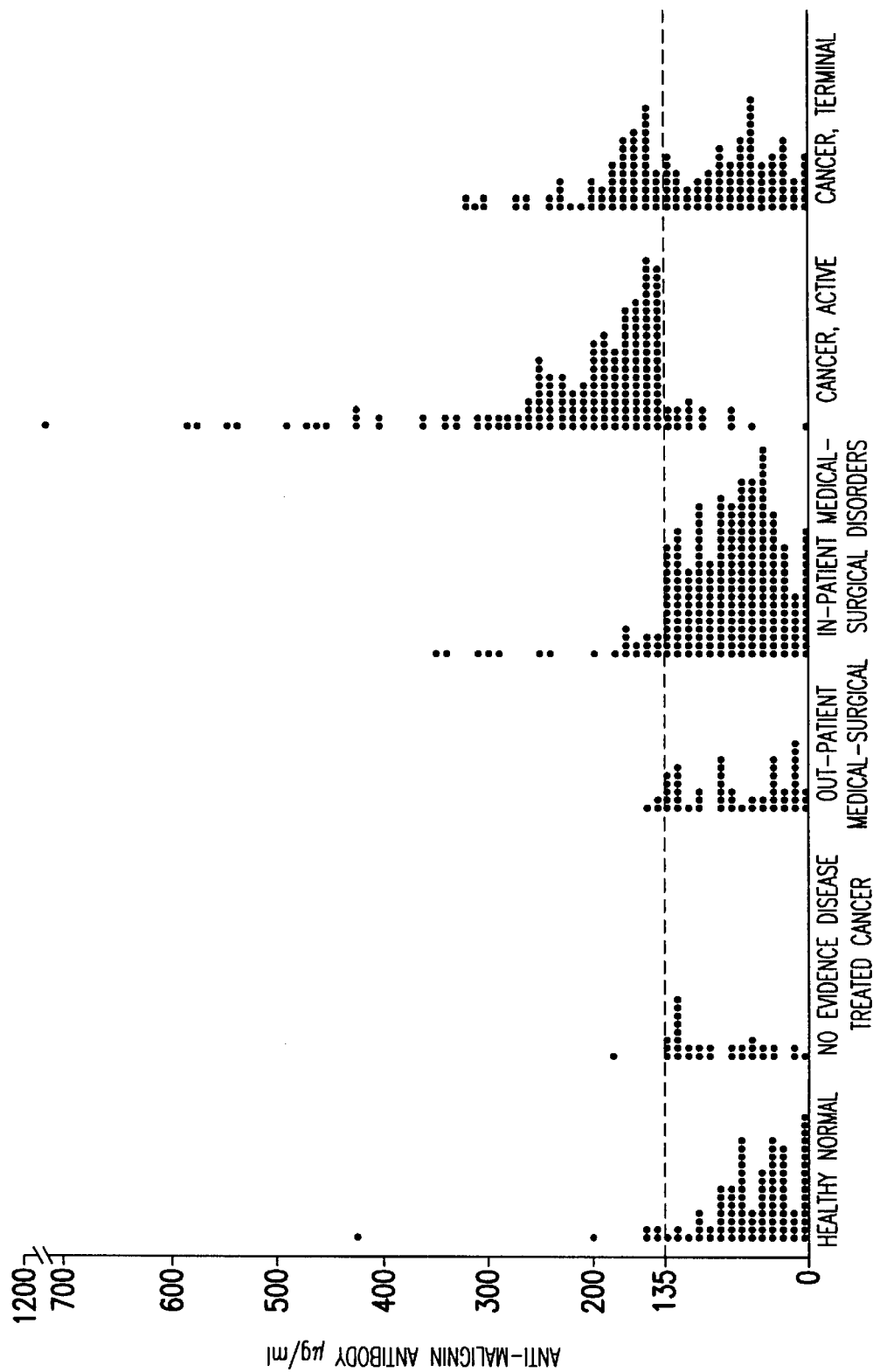
FIG. 3 is a plot of the concentration of anti-malignin antibody in healthy control subjects, treated cancer subjects, active cancer subjects, and terminal cancer subjects.

The Example 10B terminal cancer patients had anti-malignin antibody levels different from those observed in the Example 10A terminal cancer patients. In Example 10B, 80% of the sera from terminal patients contained normal antibody concentrations whereas only 52% of the terminal patients in the Example 10A studies contained such antibody concentrations. Additionally, both the mean concentration of anti-malignin antibody (84 u g/ml) and the mean survival time of the Example 10B terminal patients (2.8 months) were lower than those observed in the Example 10A studies (122 u g/ml and 4.4 months, respectively). This observation may be due to the fact that the cancers in the present terminal patient group were generally far more advanced in the Example 10B study than those observed in the Example 10A study. Nevertheless, as shown in FIG. 3, the anti-malignin antibody concentration frequency for each group of patients (healthy normal, no present evidence of, but formally treated for cancer, out-patient medical-surgical, in-patient medical-surgical active cancer and terminal cancer) was essentially identical in the study of both Example 10A and 10B. This observation is important because the type and source of the malignancies in the two studies differed. In Example 10B study, 0.7% of the patients had brain cancer whereas 27% of those in Example 10A had brain cancer. On the other hand, 12% of the Example 10B population were melanoma patients compared to only 3% in the Example 10A study. Thus, regardless of the nature of the cancer, anti-malignin antibodies are correlated with the stage of the cancer (active vs. terminal) as observed in the Example 10A study. The observation that the level of anti-malignin antibody in active cancers is independent of cell type supports the conclusion that malignin and the related cancer recognins are general antigens for transformed cells.

Additionally, patient survival did not vary in any significant manner attributable to differences in age, sex or geography.

Figure 4A:
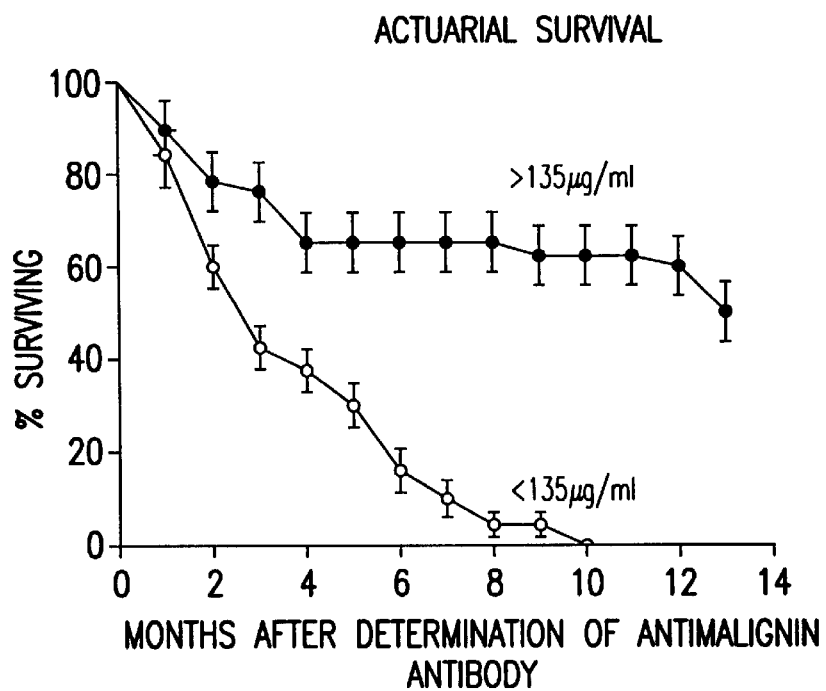
FIG. 4 is a plot of the % of subjects surviving over a period of 14 months post-determination of anti-malignin antibody serum concentrations.
Figure 4B:
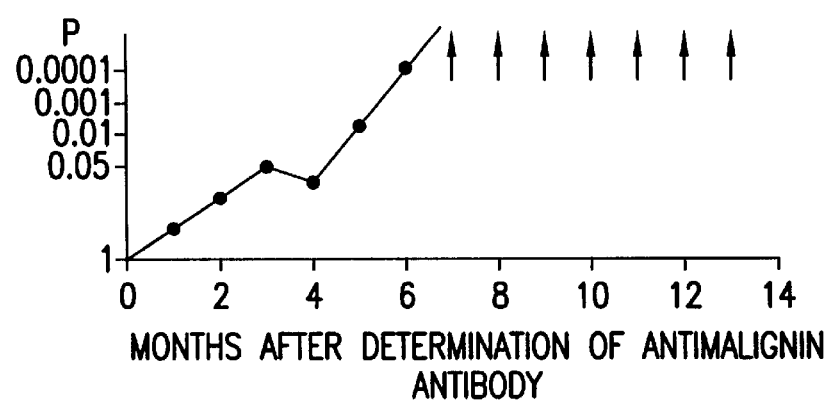

FIG. 4 shows that there is a significant difference in the survival of patients who have more than 135 m g/ml of anti-malignin antibody in their serum when compared with those who have less than 135 u g/ml serum. Restating FIG. 4, 60% of those patients whose anti-malignin antibody concentration was greater than 135 were alive 1 year later whereas there were no survivors after 10 months among those patients whose anti-malignin antibody concentration was less than 135. FIG. 4 also shows the standard error for each of its data points. After 5 months, the difference in survival between those patients having more than 135 and those patients having less than 135 was significant at the $P<0.01$ level and beyond 6 months they were significantly different at the $P<0.0001$ level.

Figure 5A:
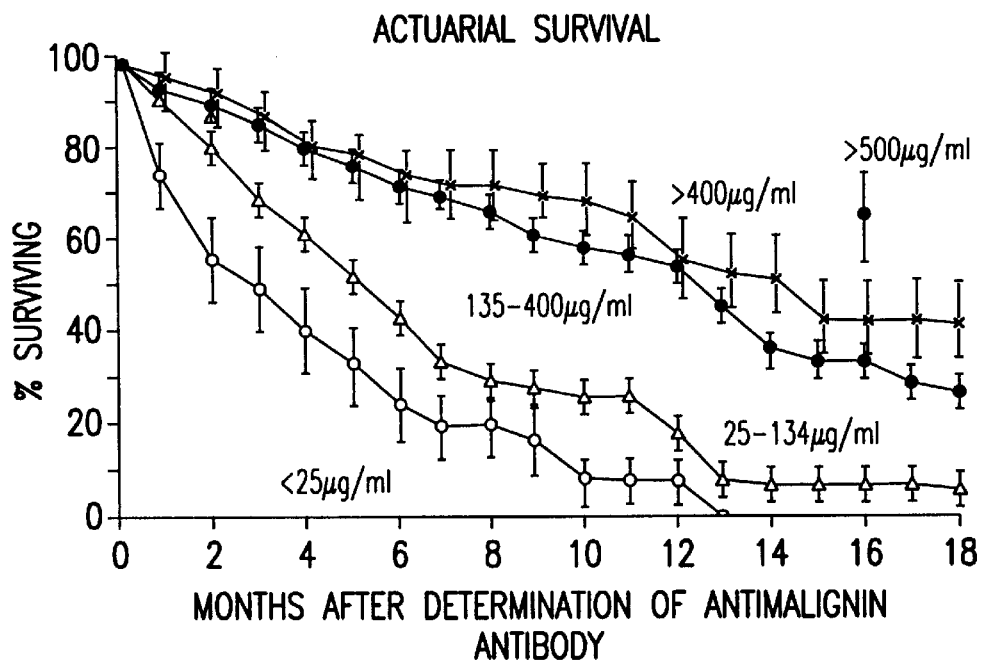
FIG. 5 is a plot of % survival of patients over a period of 18 months post-determination of serum anti-malignin antibody.
Figure 5B:
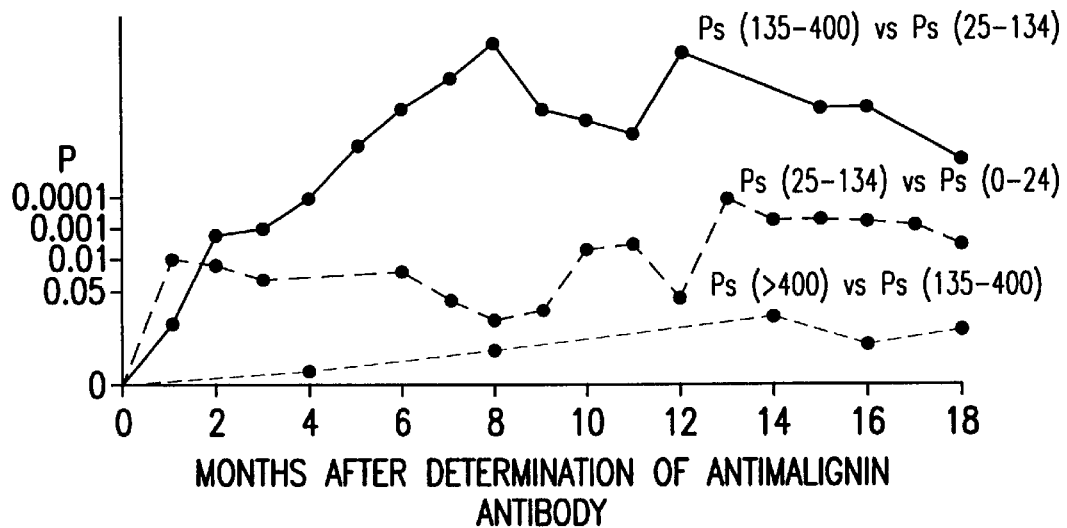

As the data from the Example 10A and the Example 10B studies are comparable, the results for both of these studies are combined, and presented in FIG. 5. The large number of patients in the combined Example 10A and Example 10B studies (N=511) permitted a more detailed statistical analysis of the correlation between anti-malignin antibody concentration and survival. For this analyses, the complete set of data was divided into 4 groups. The first group, labelled <25, represents those patients whose anti-malignin antibody concentration was less than 25 micrograms per ml serum (N=45). After 8 months, only 20% of the <25 group survived and none of this group survived beyond 13 months. The second group, that labelled 25–134 had been between 25 and 134 micrograms anti-malignin antibody per ml (N=144). The third group labelled 135–500, had between 135 and 400 micrograms of anti-malignin antibody per ml of serum (N=246), and the fourth group, labelled >400, had more than 400 micrograms anti-malignin anti-body per ml of serum (N=66). As can be seen in FIG. 5, as the concentration of anti-malignin antibody increases, so does the fraction of patients surviving. Specifically, 72% of the >400 group survived to 8 months and over 40% of this group survived 18 months. In fact, 65% of a small subgroup of the >400 group—those with more than 500 micrograms anti-malignin antibody per ml serum (N=20)—survived through 20 months.

Statistically, the difference in survival between the <25 and the 25–134 group was statistically different at the $P<0.05$ level from the 10th month onward. The difference between the 25–134 group and the 135–400 group was significant at the 0.001 level, or better, from the third month onward. However, the difference between the 135–400 group's survival and that of the >400 group was only marginal. Nonetheless, the smaller subgroup of the >400 group—the <500 micrograms per milliliter group—was statistically different from that of those patients whose anti-malignin antibody concentration was between 400 and 499 micrograms per milliliter at 20 months at the $P<0.01$ level.

Thus, the relationship between anti-malignin antibody concentration and survival demonstrates that high concentrations of this antibody reliably predict long survival.

Considering the fact that death from cancer can be due to many proximal causes such as hemorrhage, infection and failure of vital organs, the correlation to survival for one property, the concentration of anti-malignin antibody, indicates that it may play a central role, or at least be a consistent epiphenomenon at certain stages in the progression of cancer.

The present data suggest that in addition using anti-malignin antibody concentration as a diagnostic aid based upon its elevated levels as early as 19 months before there is clinical evidence of cancer, anti-malignin antibody may be useful in monitoring the progress of diagnosed cancer patients. Anti-malignin antibody appears to be the only antibody quantitatively related to survival in cancer patients.

Moreover, the present data suggests that the administration of anti-malignin antibody may be therapeutic. A general anti-cancer antibody with specificity for malignant cells that is not restricted by the type of cancer cell has apparent advantages.

Legend for FIG. 3
EXAMPLE 10B

FIG. 3 is a superimposition of the results from EXAMPLE 10B onto those from EXAMPLE 10A. The EXAMPLE 10B anti-malignin antibody concentrations, the dark dots (●), are superimposed upon those found in EXAMPLE 10A, which are the lighter dots. (The EXAMPLE 10A data is a reproduction of FIG. 1 coupled with the FIG. 2A, cancer, Terminal data). The EXAMPLE 10B mean values are indicated by dark horizontal bars (—) and the EXAMPLE 10A mean values are lighter double dashes (--).

Legend for FIG. 4
EXAMPLE 10B

Actuarial survival of cancer patients grouped according to their concentration of anti-malignin antibody, above (●) and below (○) 135 micrograms/ml (Series II). P, the probability, indicates the level of significance for the difference between the two curves at each month. The arrows indicate that the value for P continues to rise beyond P<0.0001 level after 6 months.

Legend for FIG. 5

EXAMPLE 10A

Actuarial survival of cancer patients grouped according to their concentration of anti-malignin antibody, <25 mg/ml ○, 25–134 mg/ml Δ, 135–400 mg/ml ●, above 400 mg/ml x, and the subgroup of those above 400 whose antibody concentration was above 500 mg/ml (Combined series I and II). P, the probability, indicates the level of significance of the difference between the probabilities of survival, Ps, by month, for each of the pairs of groups being compared, e.g., Ps (135–400) vs. Ps (25–134).

EXAMPLE 11

Diagnosis of Tumor Cells by Immunofluorescence

The compounds Anti-Astrocytin, Anti-Malignin, and S-TAG have been shown to attach preferentially to tumor cells. This specificity permits use of these compounds to diagnose tumor cells in histology sections by conjugating dyes or radioactive substances to Anti-Astrocytin, Anti-Malignin, or S-TAG. Standard labeling techniques may then be used. A procedure using S-TAG is as follows.

One procedure which has been found satisfactory is a modified St. Marie procedure. Human brain tumor specimens are frozen and 5 micron thick sections cut. These are stored in a moist container at minus 70° C. 4 to 8 weeks before staining. The conjugate may be a standard anti-serum such as goat anti-rabbit conjugate. The conjugate is labeled by techniques known in the art with fluoresein or other labeling substance. Fluorescein labeled goat anti-rabbit conjugate as commercially available may be used. The fluorescent technique used was a standard one in which a 1:200 to 1:400 solution of TAG is incubated for about 30 minutes or more on the tumor section, followed by washes to remove unattached TAG. Three washes with phosphate buffered saline has been found satisfactory. Conjugate incubation with fluorescein-labeled conjugate followed by washes is then performed, followed by microscopic inspection. Normal cells and their processes fail to stain both in tumor sections and in control sections of normal non-tumor brain. Fluorescence is brightly present in tumor glial cells and their processes.

EXAMPLE 11A

Detection of Non-Brain Malignant Cells with Fluorescent Signal From TAG

The uses of TAG products coupled with a signal emitter such as a dye or a radioactive label to detect cancer cells is described, for example, at pages 12–18 and EXAMPLE 11 herein. In this EXAMPLE 11A, the detection of non-brain malignant cells is described.

As described in EXAMPLE 10 utilizing human serum in the determination of TAG, after the anti-malignin antibody was bound to the immobilized antigen and non-bound serum proteins washed away, the antibody was cloven from the binding with 0.25M acetic acid at 37° C. for 2 hours and the TARGET reagent separated from it by centrifugation. The TAG antibody solution was quantitated by means of its absorption at 280 mμ. The TAG solutions were stored at −20° C., then thawed and combined, brought to pH 7 by titration with 6N NaOH, dialyzed against phosphate buffered saline pH 7, filtered and concentrated on Millipore Pellicon 1000 membranes, centrifuged to clear insoluble protein and the immune globulin complexes concentrated and freed of immunologically non-active compounds by Cellex D and Blue Sepharose CL6B (Pharmacia) chromatography. This human anti-malignin antibody reacts with anti-human gamma globulin in Ouchterlony double diffusion. When TAG is used with fluorescein conjugated to anti-human gamma globulin in standard double layer Coons immunofluorescence it stains malignant glia, breast carcinoma, ovarian carcinoma, adenocarcinoma of colon, and other types of cancer cells in postoperative and biopsy tissue sections, as well as in human sputum, bronchial washings, pleural effusion fluid, gastric aspirate and bladder urine. The concentration of protein in TAG which yield clear fluorescence when controls are negative, is 1 to 10 μg per section.

The production of a "purified" TAG was undertaken by reacting the sera from patients with a variety of cancers with bromoacetylcellulose-MALIGNIN by methods earlier described (EXAMPLE 8). The antibody bound in this reaction was cleaved with 0.25M acetic acid, quantified by measurement at O.D. 280 using a conversion factor of 1.46 for gamma globulin frozen and stored at −20° C. This antibody was found to contain immunoglobulin as determined by anti-human gamma-globulin antiserum specific for gamma chains (BioRad Laboratories, Inc.) and with anti-FAB and anti-Fc fragments (Miles Laboratories). It also reacts with rabbit anti-human albumin (BioRad Laboratories).

It was found that whereas 10 to 50 micrograms of protein TAG are required to produce specific immunofluorescent staining of cells which contain Malignin, only 1 to 10 micrograms of purified protein TAG are required for this specific staining in all sections, and in a few, less than one microgram has been found to suffice.

At was found that the most active preparation of purified TAG is that which is eluted with the highest ionic strength elution, i.e., from 0.15M to 1.5M. Any method of production which uses this fact is useful; three preferred methods are given below.

Method I—Fractionation of TAG chromatography with DEAE cellulose (Cellex D, BioRad Laboratories) was first employed with step-wise elution with increasing ionic strength and decreasing pH, the same sequence of eluants as that given in Example I for the production of Crude Astrocytin-Precursor-Containing Fraction. Good separation was obtained of the bulk of the protein into three fractions, Peak I obtained with Solution 1 (see Example 1) and Peak II obtained with Solution 1 (see Example 1) and Peak II obtained with Solution 6 and Solution 7. Ouchterlony double diffusion showed the TAG in Peak I still to contain appreciable protein with albumin mobility, and while Peak II contained most of the albumin, appreciable IgG could be detected. Rechromatography of Peak I gave a progressively pure IgG until, after the seventh chromatography, essentially no albumin (less than 3%) could be detected by Ouchterlony gel diffusion in which 5 to 10 micrograms of human albumin was detectable with rabbit anti-human albumin. The IgG so obtained was prone to denaturation and loss of immunological reactivity after a few days standing at 0°–5°C.

Method II—A second fractionation of TAG was made with chromatography on Sepharose CL-6B (Pharmacia, Inc.) starting with low molarity buffer (0.0005M phosphate) and proceeding in two steps of 0.15M and 1.5M to elute the balance of the protein. As with the Cellex D, one passage was found to be inadequate to separate, and recycling slowly improved the product. Once again, the most active fraction vis-a-vis anti-malignin antibody was in the 1.5M fraction.

Method III—Chromatography with Sepharose CL-6B next to the glass fritted disc and Cellex D layered above the Sepharose proved to be the most satisfactory method.

The graphical representation in FIG. 1 shows the fractions obtained on chromatography of TAG utilizing Method III. After the first eluate of 200 mls., 50 ml. or smaller subfractions were collected. The protein content of each eluate was determined by the optical density at 280 as with a uniform factor of 1.46 based on gamma globulin used to convert to micrograms for calculating recoveries. The absolute amount of protein requires correction in those fractions in which there is appreciable albumin. The points at which the stepwise solvent changes were made are indicated by arrows. The subfractions are designated by Roman numerals I through VIII.

The solvents corresponding to letters A–F at the arrows were as follows:

A—0.01M TRIS (pH 7.2)
B—0.05M TRIS with 0.1M NaCl (pH 7.2
C—PBS, 0.11M NaCl (pH 7.2)
D—PBS, 0.165M NaCl (pH 7.2)
E—PBS, 0.33M NaCl (pH 7.2)
F—0.05M TRIS, 1.5M NaCl (pH 7.2)

In the following Table are shown the recoveries from each fraction, a semi-quantitative determination in each of the gamma-globulin and albumin in each, as well as the activity of each fraction in the immunofluorescent staining of cancer cells. (The plus sign indicates reaction, zero no reaction and plus/Minus reaction in some cases).

EXAMPLE 12

Blind Study of Tag Specificity in Immunofluorescence

The presence of malignin was sought in cells collected from cancer patients and controls. Specimens were collected by thoracocentesis, paracentesis, bronchial or tracheal washings, sputum: and pericardial effusion, from patients with lung, breast, prostatic, colon and undifferentiated cancers, as well as from non-cancer controls including patients with emphysema, heavy smoking and epilepsy; and sputum from a former cancer patient with no evidence of disease for two years following successful treatment. Cells were concentrated by centrifugation.

The following Table shows the correlation of presence or absence of malignin in cells as determined blind by immunofluorescent staining with anti-malignin antibody (TAG), and the clinical-pathological diagnosis. The TAG stain result was correct in 20/22 specimens (91%). Standard Papanicolaou stain examinations performed blind on duplicates of these specimens by other pathologists were correct in 17/22 specimens (77%).

|  |  | CELL MALIGNIN: IMMUNOFLUORESCENCE TAG RESULTS | | |
|---|---|---|---|---|
|  |  | cancer | non-cancer | total |
| Clinical-Pathological | Cancer | 14 | 2 | 16 |
|  | Non-cancer | 0 | 6 | 6 |

TABLE

| Fraction | I | II | III | IV | V | VI | VII | VIII |
|---|---|---|---|---|---|---|---|---|
| Recovered |  |  |  |  |  |  |  |  |
| μg | 2,877 | 1,140 | 2,351 | 2,942 | 1,808 | 2,230 | 2,125 | 7,1477 |
| % | 12.5 | 5.0 | 10.2 | 12.8 | 7.9 | 9.7 | 9.3 | 32.6 |
| Immunodiffusion Against: |  |  |  |  |  |  |  |  |
| Anti-human IgG specific for gamma chains | +++ | ++ | ++ | + | ○ | + | ++ | +++ |
| Anti-human albumin | + | + | + | ++ | +++ | +++ | +++ | +++ |
| Anti-Fab | + | ++ | ○ | ++ | + | ○ | ++ | ++ |
| Anti-Fc | ++ | ++ | + | ++ | + | ○ | + | ○ |
| Immunofluorescence | ± | ± | ± | ± | ± | ± | ± | +++ |

Photographs were prepared showing the line of reaction between anti-human gamma-globulin specific for gamma chains for each of Fractions I and VIII from above.

Photographs were taken showing the use of TAG (Fraction VIII from above) to stain non-brain malignant cells) i.e., a stain of bronchogenic carcinoma cells in the bronchial washings of a patient and a stain of lymphoma cells in the pleural fluid of a patient. Non-cancer cells do not fluoresce. The TAG (1 to 10 μg in 0.1 ml phosphate buffered saline (PBS) is applied to the surface of packed cells on a glass slide incubated 30 minutes, washed three times with PBS and then layered with fluorescein-conjugated anti-human IgG diluted until non-malignant control tissues give essentially no fluorescence. The cells are visualized with a Zeiss fluorescent microscope using a tungsten lamp and filters BG 23, BG 12, and 500.

-continued

|  |  | CELL MALIGNIN: IMMUNOFLUORESCENCE TAG RESULTS | | |
|---|---|---|---|---|
|  |  | cancer | non-cancer | total |
| Diagnosis | Total | 14 | 8 | 22 |

In addition to the positive stain for malignin in cells from breast, ovarian and bronchogenic carcinoma, and astrocytomas, cells grown in tissue culture from human squamous cell carcinoma of the vulva, and from five different types of human lymphoma, as well as leukemic cells in both acute and chronic leukemia blood have demonstrated positive staining. Melignin was visualized and photographed in a variety of human cancer cells by anti-malignin antibody double-layer immunofluorescence. The second layer fluorescein-labelled anti-antibody was diluted in control experiments to as much as 1:1,600 until non-specific fluorescence was completely eliminated in the absence of the first layer anti-malignin antibody. Under these conditions, anti-malignin antibody was active at one nanogram antibody protein per cancer cell in producing the specific immunofluorescence seen and photographed in: A- bronchogenic carcinoma cells, from bronchial washings; B- lymphocytic leukemia cell, from blood; C- ovarian carci- Procedure for Antigen-Antibody Reaction A portion of the labeled solution was also plated on an Ouchterlony gel plate to determine its ability to react with malignin in the antigen-antibody reaction. After a 3-hour period, the resulting sharp reactive lines were removed from the gel and their content of radioactivity measured. An equal portion of the gel not involved in the reaction was also removed and its content of radioactivity was also measured as background.

Results

Labeling Efficiency

TABLE 1

Labeling Efficiency of $^{99m}$Tc-TAG-1 and $^{99m}$Tc-TAG-2

| COMPOUND | SITE ON PAPER | CPM | % | CHEMICAL SPECIES |
|---|---|---|---|---|
| NaTcO$_4$-$^{99m}$Tc | origin | $4.94 \times 10^5$ | 7.33% | reduced TcO$_4$- |
| NaTcO$_4$-$^{99m}$Tc | solvent front | $6.25 \times 10^6$ | 92.67% | TcO$^{4-}$ |
| TAG-1 | origin | $4.35 \times 10^6$ | 98.47% | TAG-$^{99m}$Tc |
| TAG-1 | solvent front | $6.76 \times 10^6$ | 1.53% | TcO$_4$- |
| TAG-2 | origin | $1.96 \times 10^6$ | 98.01% | TAG-$^{99m}$Tc |
| TAG-2 | solvent front | $3.98 \times 10^6$ | 1.99% | TcO$_4$- | noma cells, at surgery; D- squamous cell carcinoma (2 cells), grown in tissue culture; E- astrocytoma, anaplastic, at surgery.

EXAMPLE 13

Detection of Cancer Cells with Radioisotope Signal From TAG

In this Example, the feasibility of attaching a radioactive label to TAG is demonstrated. Second, the injection into animals of this radio-labeled TAG has been accomplished and shown to be safe and effective. Third, the radio-labeled TAG localized preferentially in the cancer tissue when compared to normal tissue, thus indicating that the specificity previously demonstrated in vitro of the preference for cancer cells which is conveyed by the use of specific anti-Malignin TAG products is confirmed in vivo.

The Labeling of TAG with 99m Technetium ($^{99m}$Tc)

Procedure for Labeling

1. Two preparations of TAG were used, here designated TAG-1 and TAG-2. TAG-1 and TAG-2 (concentration of each 0.4 mg/0.5 ml) were added to separate sterile evacuated vials.
2. To each vial was added 0.1 ml of a stannous chloride solution (10 mg SnCl$_2$. 2 H$_2$O in 100 ml of 0.01N HCl). The vials were mixed for 3–4 minutes.
3. 0.1 ml. (6mCi) of $^{99m}$Tc-pertechnetate (sodium salt) was added and mixed 2–3 minutes.

Procedure for determining labeling efficiency

Samples of the $^{99m}$Tc-TAG-1 and $^{99m}$Tc-TAG-2 were tested for labeling efficiency by descending paper chromatography using Watman No. 1 paper with 85% methanol as the solvent. A similar study was done with Sodium Pertechnetate-$^{99m}$Tc which acted as a control.

After 2 hours, the papers were removed from the chromatography tank and divided in two sections: (1) 1 cm about the origin; (2) the remaining paper up to the solvent front. Each section was then counted in a gamma well scintillation counter and its content of radioactivity determined (cpm)

Approximately 50 labda were plated on each paper strip.

TABLE 2

| GEL AREA | ANTIGEN-ANTIBODY RESECTION COUNTS PER MIN. | % |
|---|---|---|
| TAG-2 line | $1.99 \times 10^6$ | 92.04% |
| Background gel | $1.72 \times 10^5$ | 7.96% |

Conclusions

The following conclusions were reached relative to the quality control tests employed:

1. $^{99m}$Tc-pertechnetate was reduced by stannous chloride to a more reactive oxidation state (+4+5).
2. The reduced pertechnetate labeled both the TAG-1 and TAG-2 preparations.
3. The $^{99m}$Tc-TAG-2 was tested for its ability to retain its activity and was found to retain its ability to react immunologically.

The Use of Radio-Libeled TAG in vivo to Detect Cancer Cells

Wistar rats were injected intracerebrally with C6 glioma tumor cells which had had previous passages in rats and in tissue culture. The rats were observed for the first signs of growing tumor, such as weakness, tremor or unsteadiness. These symptoms first appear seven to 10 days from injection, and with fast growing tumors result in death within three to four days in many animals, and one week in all. As soon as symptoms appeared, the animals were injected with labeled TAG intravenously in the tail vein, then the animal anesthetized at varying times, the brain removed, the tumor dissected from of normal brain, and the radioactivity in each dissected specimen compared.

Preliminary $^{99m}$Tc-TAG experiment

| Animal | Sacrifice (hr. post injection) | Tumor wt., mg. | Counts/gm/min. Tumor | Normal Brain |
|---|---|---|---|---|
| A | 1.25 | 1.9 | 149,100 | 13,400 |
| B | 5.30 | 6.0 | 16,200 | 6,600 |
| C | 7.21 | 23.0 | 53,000 | 5,800 |
| D | 24.10 | 29.0 | 66,700 | 7,500 |

Tumor and normal brain specimens were counted overnight in the gamma-well counter. All samples and standards were decay corrected for convenience to the mid-count of the first sample in the sequence.

Conclusion

The preferential localization of radioactivity in tumor as compared to normal tissue is demonstrated above.

EXAMPLE 14

Production of Monoclonal Anti-Malignin Antibodies, MAMA-S, MAMA-F, and MAMA-FS, and their Respective Novel Producer Cells A myeloma cell line (P3x63-Ag-8) was cultured in Dulbecco's minimum essential medium supplemented with 10% fetal bovine serum ($D_{10}$), in a humidified incubator at 37° C. and 5% $CO_2$.

Inbred female BALB/cJ mice (8 weeks of age) (Jackson Laboratory, Bar Harbor, Me.) were immunized intraperitoneally, 4 times at weekly intervals with 1 mg Malignin emulsified in complete Freund's adjuvant (Difco). Sera of the immunized mice were tested for the presence of anti-melignin antibody and antibody positive mice were further boosted 4 days prior to cell fusion.

Immune spleen cells ($10^8$) were fused with the myeloma cell ($10^7$) using polyethylene glycol (PEG, 1000, J. T. Backer) as the fusion inducing agent as described by Galfre et al (Nature 266, 550–552, 1977). The PEG treated cell mix was seeded into 96 wells of a microtiter plate (Costar 3596) in $D_{10}$ supplemented with hypoxanthine, aminopterin, and thymidine ($D_{10}$ HAT) (Littlefield, J. W., Science 145: 709, 1964). About one half of $D_{10}$ HAT was replaced twice weekly for two weeks. The spleen cells did not survive in vitro, while the unfused myeloma cells were killed in $D_{10}$ HAT. Only the hybrid cells remained actively growing after 10 days under the selective conditions. After two weeks in $D_{10}$ HAT, the hybrid cells were fed with medium the same as $D_{10}$ HAT except with the omission of aminopterin ($D_{10}$ HAT) for another week, then with $D_{10}$. Whenever the wells were about 80% covered by hybrid cells, supernatants were aspirated for anti-malignin antibody assay.

Cells from the antibody producing wells were cloned in soft agarose by modifications of the method as described by Cotton et al (Eur. J. Immunol. 3, 135–140, 1973). Briefly, an equal volume of warm 0.8% agarose (Seaplaque, Marine Colloid Inc.) and double strength $D_{10}$ were mixed and plated 2 ml to a 60 mm dish and chilled at 4° C. for 15 minutes as base layer. One thousand cells in the same medium were overlayered on the baselayer and chilled, ten incubated in-the same conditions as regular cell cultures. The anti-malignin antibody positive clones were further grown as ascitic tumors in BALB/cJ.

TABLE

EXAMPLE 14
Quantity of Antibody (μg/ml extracellular fluid) for Each

| Extra-Cellular Fluid | Months After Manufacture of PRODUCER CELLS | | Antibody Producing Clone | | | | |
|---|---|---|---|---|---|---|---|
| | | | MAMA-F | | MAMA-S | | MAMA-F/S |
| Cell | 1 mo. | 38 | 32 | 22 | 27 | 21 | 25/21 |
| Supernate | | 67 | 32 | 38 | 37 | 27 | 21/21 |
| | | 19 | 42 | 27 | 53 | 21 | 21/19 |
| | | 27 | 30 | 55 | 62 | 25 | 25/23 |
| | | 25 | 21 | 27 | 32 | 23 | 29/27 |
| | | 26 | 29 | 37 | 26 | 44 | 48/45 |
| | | 52 | 23 | 29 | 34 | 33 | 2/18 |
| | | | | | | 30 | |
| Cell | 3 mo. | 51 | | 16 | | | 41/34 | 41/39 |
| Supernate | | 136 | | 15 | | | 36/36 | 29/23 |
| | | 73 | | 16 | | | 47/41 | 39/37 |
| | | 44 | | 29 | | | 39/33 | 30/27 |
| | | 32 | | | | | 62/58 | 22/22 |
| | | 30 | | | | | 101/110 | 15/18 |
| | | 23 | | | | | 30/29 | 18/18 |
| Cell | 4 mo. | 19 | 30 | 18 | 18 | | 30/34 | 32/29 |
| Supernate | | 32 | 30 | 26 | 23 | | 15/16 | 21/23 |
| | | 30 | 27 | 25 | 27 | | 27/26 | 23/21 |
| | | | 27 | 29 | 30 | | | |
| | | | | 30 | 29 | | | |
| Cell | 5 mo. | 126 | 140 | 34 | 88 | | 47/97 | 49/82 |
| Supernate | | 178 | 393 | 248 | 69 | | 22/27 | 74/178 |
| | | 162 | 296 | 89 | 114 | | 26/30 | 83/149 |
| | | | | 92 | 123 | | 56/127 | 94/232 |
| | | | | | | | 308/82 | 112/79 |
| | | | | | | | 62/107 | 56/169 |
| | | | | | | | 161/390 | 178/164 |

TABLE-continued
EXAMPLE 14
Quantity of Antibody (μg/ml extracellular fluid) for Each

| Extra-Cellular Fluid | Months After Manufacture of PRODUCER CELLS | Antibody Producing Clone | | |
|---|---|---|---|---|
| | | MAMA-F | MAMA-S | MAMA-F/S |
| | | | 249/301 | |
| Mouse Ascites Fluid | 8 mo. | | 660/1,070 780/670 | |

(F = fast reacting, in 10 minutes;
S = slow reacting, in 2 hours;
FS = both types of antibody produced/Method as in EXAMPLE 10)

The above Table shows the quantities of monoclonal anti-malignin antibody prod-aced by each antibody producing clone, in micrograms of protein per ml of extracellular fluid. The yields of antibody are seen to be good for the first four months of propagation of the clones, and to have increased by the fifth month of propagation. The cells continued to grow well through the eighth month and to successfully grow when transferred intraperitoneally to the mouse, where the yield of antibody again increased as expected to as much as 1 mg. of MAMA-S per ml of ascites fluid. The cells also grew successfully on soft agar and where frozen and stored in liquid nitrogen and grown again after thawing. Aliquots of each clone where frozen in liquid nitrogen for permanent storage and regrowth at later dates.

The monoclonal antibody in each case was quantified as protein by optical density at 280 millimicrons, was non-dialyzable and migrated on SDS-polyacrylamide gel electrophoresis predominately as gamma chain immunoglobulins.

With progressive recloning, each specific monoclonal antibody producing cell was concentrated. Thus, recloning of MAMA-B Producer Cells yielded four out of six colonies which were MAMA-B Producers, and recloning of MAMA-A Producer Cells yielded three out of four colonies which were MAMA-A Producers.

Each of the three types of antibody stained a wide range of malignant cells by immmunofluorescence in approximately the same concentration range as previously observed with purified TAG products. That is, one nanogram of antibody protein stained one cancer cell. Photographs were taken of specific immunofluorescent staining obtained with human leukemic blood, both acute and chronic, six cultured lined of leukemia cells (JY, KARPAS, CEM, RAJI, HL60, and K562), and three human lymphomas. Staining was obtained with MAMA-F, MAMA-S and MAMA-FS.

Second layer staining with fluorescent labels, both fluorescein and rhodamine, at concentrations as low as 1:1,600 was observed and recorded. These very law concentrations of the second layer permitted dilution until background non-specific staining was eliminated, and at those concentrations of second layer (FITC or rhodamine) highly specific staining was obtained with MAMA-F, MAMA-S and MAMA-FS.

EXAMPLE 15

Demonstration by Cytofluorography of a Diagnostic "Malignin Fluorescent Index" with Monoclonal Anti-Bodies F & S Using the two monoclonal anti-malignin antibodies, MAMA-F and MAMA-S, in several concentrations, time of incubation, washing or no washing, different concentrations and time of incubation of fluorescein isothiocyanate anti-mouse antibody (FITC), and other specifications as to method of preparing blood and/or white cells, in both normal and cancer sera (leukemias, lymphomas), in a study of how these antibodies may best be used with flow cytometry instruments, the following conclusions and preferred examples are discussed:

1. By quantitating the actual number of cells fluorescing per 100 cells counted and correcting for the cells fluorescing without MAMA but with the FITC antibody alone, an absolute number is obtained which represents the true or specific fluorescence due to MAMA. Thus,
   Malignin Fluorescent Index=(Number of Cells fluorescing with MAMA plus FITC) less (Number of cells fluorescing with FITC alone)
2. The Malignin Fluorescent Index is a rapid diagnostic test for malignant cells in fluid suspension, which distinguishes normal from malignant cells regardless of the cell type (malignin is a general transformation antigen which relates to the process of malignant transformation rather than the cell type).
3. Examples from the data obtained:

| Date + Specimen | MAMA Used | Time, mih. | Washed +/− | FITC min. | Cells fluorescing/100 corrected | | | Specific Total | Malignin Fluorescent Index |
|---|---|---|---|---|---|---|---|---|---|
| | | | | | Region 2 | Region 3 | Region 4 | | |
| 4/29/81 | | | | | | | | | |

-continued

| Date + Specimen | MAMA Used | Time, mih. | Washed +/- | FITC min. | Cells fluorescing/100 corrected | | | Malignin | |
| | | | | | Region 2 | Region 3 | Region 4 | Specific Total | Fluorescent Index |
| --- | --- | --- | --- | --- | --- | --- | --- | --- | --- |
| Normal | 0 | 20 | 0 | 30 | 4.1 | 13.3 | 36.5 | | |
| Normal | MAMA-F specific | 20 | 0 | 30 | 3.5 −0.6 | 12.3 −1.0 | 31.7 −4.8 | −6.4 | |
| Leukemia (L) | 0 | 20 | 0 | 30 | 11.8 | 7.8 | 3.0 | | |
| Leukemia (L)(Acute) | MAMA-F specific | 20 | 0 | 30 | 15.14 +3.5 | 7.8 0 | 3.2 +0.2 | +3.8 | +10.2 |
| Normal | 0 vs. MAMA-S | 60 | + | 10 | −5.4 | −0.2 | +1.6 | −4.0 | |
| Leukemia (L) | 0 vs. MAMA-S | 60 | + | 10 | +0.8 | +0.3 | −0.2 | +1.3 | +5.3 |
| Leukemia (VH) Chronic | 0 vs. MAMA-S | 60 | + | 10 | −2.7 | −14.1 | +0.5 | −16.3 | −12.3 |
| Lymphoma (S10) | 0 vs. MAM-S | 60 | + | 10 | +0.1 | +0.4 | +11.8 | +12.3 | +16.3 |
| Lymphoma (S15) | 0 vs. MAMA-S | 60 | + | 10 | −0.5 | −0.3 | +6.1 | +5.3 | +9.3 |
| Lymphoma (S16) | 0 vs. MAMA-S | 60 | + | 10 | −0.5 | −0.2 | +4.5 | +3.8 | +7.8 |

EXAMPLE 16

Demonstration that Anti-Astrocytin, Anti-Malignin and S-TAG are Cytotoxic to Tumor Cells Growing in Tissue Culture.

Standard tests for determining cytotoxicity may be used. Generally, the number of cells in a fixed counting chamber, usually to contain about 100 live cells, is counted. These cells are then treated with the agent being tested and the number of cells which are still alive is counted.

In a standard test of cytotoxicity of S-TAG Solution obtained in accordance with the methods of EXAMPLE 9 against cells in tissue culture derived from a patient with a glioblastoma Grade III-IV, well characterized as of glial origin, S-TAG produced death of all cells in the counting chamber even when in high dilution of 1:00 and 1:1003, representing as little as 0.2 and 0.02 µg of S-TAG per ml. of solution. Similar results are obtained with high dilutions of Anti-Astrocytin and Anti-Malignin.

Both the specificity exhibited in EXAMPLE 11, 11A, 12, 13, 14 and 15 and the cytotoxicity demonstrated in this EXAMPLE and EXAMPLE 17 are highly relevant to the therapeutic possibilities of Anti-Astrocytin, Anti-Malignin and S-TAG for malignant tumors in man. The practical diagnostic potential of both of these phenomena for tumor tissue removed at operation but requiring diagnosis by histology is already demonstrated herein.

EXAMPLE 17

Demonstration of Cytotoxicity of a Mixture of Monoclonal Anti-Malignin Antibodies MAMA-F and MAMA-S Whereas either MAMA-F or MAMA-S alone does not produce appreciable cytotoxicity with malignant cells, when combined, the admixture of these two monoclonal antibodies is actively cytotoxic to malignant cells. In addition, the product MAMA-FS is cytotoxic. The admixture of MAMA-F and MAMA-S and the product MAMA-FS are cytotoxic at approximately the same concentrations as previously observed for Anti-Astrocytin, Anti-Malignin and S-TAG products (EXAMPLE 16), i.e. approximately one nanogram of antibody per cell results in lysis of the cell.

Cytotoxicity also was observed and recorded on both the Coulter cytofluorograph and on the Ortho cytofluorograph, each instrument measures an absolute viable cells count at a point in time. Destruction of viable malignant cells e.g. pancreas, leukemic and lymphoma carcinoma was observed over a period of 15 to 60 minutes. Malignant cells which were destroyed by either the mixture of MAMA-F and MAMA-S or by MAMA-FS scattered light and fluoresced at a specific, measurable wavelength. Killing cancer cells is, by definition, a therapeutic process. Consequently, products which kill these cells are therapeutic products.

EXAMPLE 18

Human spleens which had been surgically removed from non-cancer (thalassenic) patients were disected as free as possible of other tissue. A fraction of a spleen was minced in neutral buffer, e.g. 0.0005M pH7 phosphate buffer. The mincing was performed at a reduced temperature to segregate the lymphocytes from other material, the minced admixture was passed through a nylon net filter. The lymphocytes in the filtrate were then separated by a Ficoll/Hypaque gradient.

The resulting lymphocyte admixture was cultured for a week in RPMI 1640 containing HEPES and glutamine, and 10% fetal calf serum. Thereafter, the cell culture supernate was tested for the presence of anti-malignin antibody by immunoabsorption.

Specifically, malignin was covalently bound to bromoacetylcellulose (BAC) to produce immobilized malignin (BAC-malignin). Lymphocyte culture supernate, 0.4 ml at 0⁻ C., was added to 0.2 ml of BAC-malignin. The 0.2 ml BAC-malignin contained approximately 20 micrograms of immobilized malignin, which was an excess of antigen. The resulting BAC-malignin-anti-malignin antibody complex was washed three times with cold saline. To remove the bound antibody, the complex was then incubated with 0.25M acetic acid at 37° C. for two hours, centrifuged at 3,000 rpm in a Beckman desk top centrifuge for 20 minutes, and the optical density (O.D) of the clear acetic acid supernate was read at 280 nanometers. The O.D. was converted to micrograms antibody protein per ml culture supernate using a 1.46 gamma globulin conversion factor.

Additionally, the anti-malignin antibody heavy chains were characterized by SDS-PAGE electrophoresis. The acetic acid supernate was neutralized, concentrated by pre-evaporation to a concentration of approximately 200 ug/ml and reduced with dithiothreitol so as to liberate the heavy chains. Thereafter, the anti-malignin antibody heavy chains were examined by standard SDS-polyacrylamide gel electrophoresis (SDS-PAGE). Also on the same electrophoretic gel in vivo produced anti-malignin antibody heavy chains were characterized. The electrophoresis showed that the heavy chains from both the in vivo and the in vitro produced anti-malignin antibodies were predominantly of the mu type having molecular weight in the range of about 70K to about 80K Daltons. These data suggest that anti-malignin antibody is an IgM type antibody regardless of whether it is produced in vivo or in vitro

EXAMPLE 19

Human spleens were surgically removed from Hodgkins' Disease patients and treated in the same manner as the EXAMPLE 18 spleens were.

EXAMPLE 20

Normal human peripheral blood mononuclear cells were collected by the Ficoll/Hypaque gradient method. The B lymphocytes were then grown in culture for one week and tested for anti-malignin antibody described in EXAMPLE 18.

EXAMPLE 21

Hodgkins' Disease human peripheral blood mononuclear cells were treated according to EXAMPLE 20.

EXAMPLE 22

Pokeweed mitogen (GIBCO), 1 or 20 microliters per milliliter cell culture fluid, was added to subcultures from those EXAMPLE 18, 19, 20 and 21 lymphocytes cell cultures whose supernate contained a detectable level of anti-malignin antibody. The pokeweed mitogen did not affect the production of anti-malignin antibody by any of the lympocytes when present at a level of 1 microliter per milliliter cell culture fluid. However, 20 microliters per milliliter cell culture fluid of pokeweed mitogen stimulated the production of anti-malignin antibody in 5 out of 7 thalassemic spleen cell preparations (from less than about 10 ug/ml to 62.0±31.9 ug antibody protein/ml), in 9 out of 13 Hodgkins' Disease spleen cell preparations (from less than about 10 ug/ml to 51.7±33.3 ug antibody protein/ml), but in none of the peripheral blood lymphocyte preparations (O out of 6 normal and 0 out of 5 Hodgkins' Disease peripheral blood lymphocyte preparations). Additionally, it was also found that the ability of splenic and peripheral blood lymphocytes to produce anti-malignin antibody, both unstimulated and in the presence of pokeweed mitogen, was lost within two to four weeks of cell culture.

EXAMPLE 23

Normal, anti-malignin antibody producing, peripheral, human B lymphocytes were transformed by Epstein-Barr (EB) virus. Specifically, the lymphocytes were grown in the EXAMPLE 18 cell culture medium. Viable cell counts were performed at 4-day intervals, the cell culture medium was changed weekly, and the culture volume was adjusted to maintain a cell density of $4-5 \times 10^5$/ml as long as possible.

Separately, P3-HRIK containing EB virus cell cultures were grown in medium 1640 supplemented with 20% heat-inactivated fetal calf serum and 80 ug/ml of neomycin sulfate. When the P3-HRIK cell culture reached a cell density of about $2 \times 10^6$/ml, the spent medium was removed by centrifugation and the cells were seeded at a concentration of $3 \times 10^6$ ml in 1640 medium containing 10% heat inactivated fetal calf serum. After a period of incubation of 10–12 days at 33~ C. without media changes, the cells were removed by centrifugation at 10,000 rpm for 20 minutes, the supernatant fluid was filtered through a 0.45-u Millipore (Trademark) membrane filter and concentrated to approximately 160 ml by ultrafiltration through a Diaflo UM-10 (Trademark) membrane. The concentrated fluid was the centrifuged in a Spinco SW 25.2 rotor for 2 hours at 25,000 rpm. The pellets, consisting of subcellular components and EB virus were resuspended in growth medium containing 10% DMSO in 1/100-1/400 of the original volume of culture fluid.

To infect the lymphocytes with EB virus, a pellet of fresh lymphocytes containing approximately $4 \times 10^7$ cells was prepared. The lymphocyte pellet was resuspended in 0.3–0.5 ml of the EB virus suspension. The lymphocyte EB virus suspension was incubated for an hour at 37~ C. with frequent agitation. The cells were then washed in 20 volumes of media and planted in 8.0 ml of medium in tissue culture flasks at 37~ C. and 5% $CO_2$.

EXAMPLE 24

The EB virus transformed normal anti-malignin antibody producing peripheral human B lymphocytes produced in EXAMPLE 23 were found to continuously produce anti-malignin antibody. Moreover, the two distinct types of anti-malignin antibody previously found in human serum (e.g. EXAMPLE 10A) were both found in the transformed lymphocyte cell culture fluid.

Fast binding anti-malignin antibody production increased rapidly during the first three days for low density cultures and during the first five days for high density cultures (in both instances when the cell number was rapidly increasing). However, slow binding anti-malignin antibody production for the first five days of lymphocyte culture was minimal—⅙ to ½ that of the fast binding anti-malignin antibody production—for both high and low cell density cultures.

However, from approximately the sixth day, when the cell number tended to stabilize, slow binding anti-malignin antibody production increased. This pattern of fast and slow binding anti-malignin antibody production in relation to cell division was observed whenever the medium was renewed or the cells were grown from an aliquot frozen in liquid nitrogen.

Furthermore, the addition of 0.04 ug/ml of purified malignin peptide to growing cultures had no effect on the cell count, but was associated with an increase in the fast binding anti-malignin antibody (5.9±2.7 to 9.4±4.5 ug/ml), but only in high density cell cultures.

Electrophoretic studies showed that the transformed lymphocyte anti-malignin antibody was structurally similar to other anti-malignin antibodies in that the heavy chains isolated from both mouse monoclonal anti-malignin antibodies and human serum anti-malignin antibodies resulted in patterns similar to those obtained from transformed lymphocyte anti-malignin antibody heavy chains. Moreover, the electrophoretic patterns suggested that IgM was the predominent type of anti-malignin antibody immunoglobulin.

Additionally, SDS-PAGE demonstrated that the fast and slow anti-malignin antibody heavy chains are indistinguishable.

It was also noted that neither the fast, the slow, nor the total anti-malignin antibody produced was related to the total immunoglobulin, the total IgM or the total IgG produced.

Immunofluorescent activated cell sorting and indirect immuno-alkaline phosphatase staining of an oat cell lung carcinoma indicate that the in vitro anti-malignin antibody from transformed human lymphocytes binds in a manner similar to anti-malignin antibody from human serum.

EXAMPLE 25

The effect of various concentrations of anti-malignin antibody on small cell lung carcinoma cell growth was analyzed in vitro. Antigen-purified human anti-malignin antibody was added to 96 well tissue culture plates containing $10^4$ cells of a small cell lung carcinoma cell line (UCHNCU) cultured in suspension in RPMI medium containing 10% fetal calf serum. Serial dilutions were made of anti-malignin antibody which had been purified by absorption to immobilized malignin, (original concentration 3 to 300 mg/ml) to give a final concentration of anti-malignin to RPMI FCS of 1/6 to 1/1458. The final total volume per well was 200 ul; final concentration of anti-malignin anti-body was 100 to 24,000 picograms per cell.

The plates were incubated at 37° C. in 6% $CO_2$/air for three days. On day three cultures were pulsed with $1\mu$Ci/well of $^3$H thymidine for six hours and then harvested with an automatic cell harvester onto filter pads. The filter pads were dried for two hours in a 37° C. dry incubator, and the dried pads were placed into scintillation vials and 2 ml Optiphase scintillant was added. The vials were capped and counted on a Beckman LS 1800 Beta counter. The % inhibition of cell growth was calculated as control minus experimental/control x 100.

Figure 6:
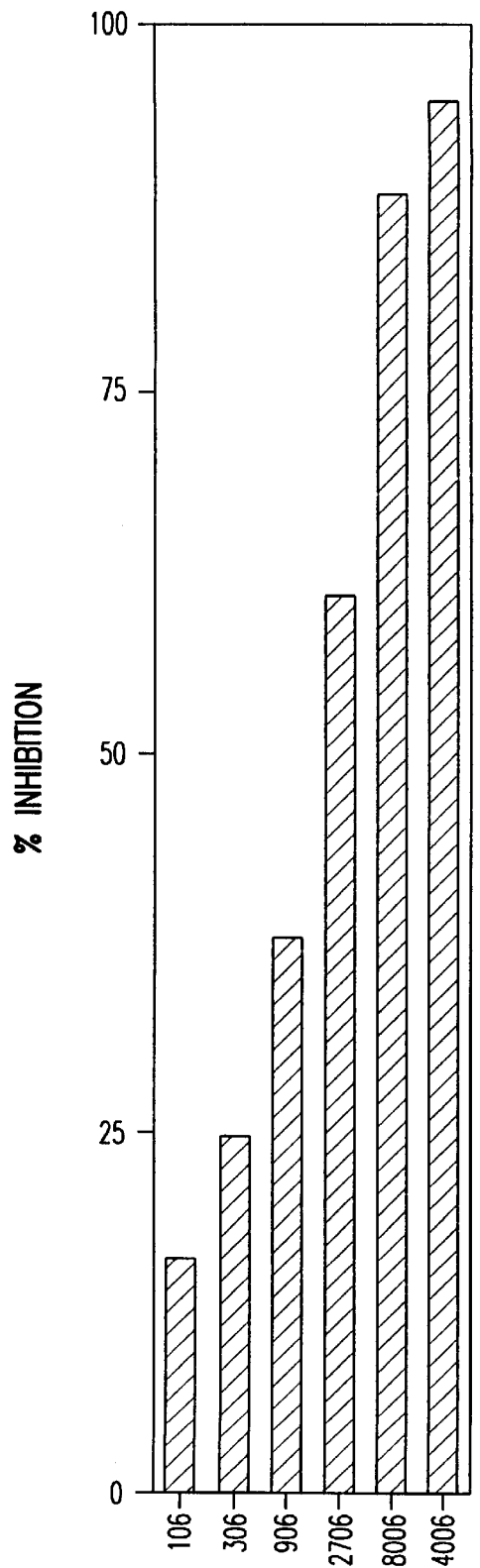
FIG. 6 is a bar graph of the % inhibition of small cell lung carcinoma cell growth per picogram/cell of anti-malignin antibody.

The results are shown in FIG. 6.

It is evident from FIG. 6 that the anti-malignin antibody is an effective cancer cell inhibitor at picogram concentrations. In view of the molecular weight of the anti-malignin IgM antibody, the effective concentration for cancer cell inhibition is femtomolar amounts.

What is claimed is:

1. A process for producing human anti-cancer recognin antibody wherein said cancer recognin is a product, derived from cancerous tumor tissue or cells, characterized by forming a single line precipitate with its specific antibody in quantitative precipitin tests and Ouchterlony gel diffusion tests, being soluble in water and aqueous solutions having a spectrophotometric absorption peak wave length of 280 mu and a molecular weight of from about 3,000 to about 25,000, and further characterized by having an amino acid residue composition characterized by high proportions of glutamic and aspartic acids and high ratios of glutamic and aspartic acids to histidine comprising the steps of:

a) obtaining a population of human lymphocyte cells;
   b) selecting a subpopulation of said population of human lymphocytes wherein said subpopulation produces anti-cancer recognin antibody;
   c) treating said subpopulation of anti-cancer recognin antibody producing human lymphocytes in a manner effective to enhance anti-cancer recognin antibody production.

2. A process according to claim 1 wherein the population of human lymphocytes is obtained by a process comprising:
   i) surgical removal of a part of a spleen; and
   ii) isolating individual lymphocyte cells from said spleen.

3. A process according to claim 1 wherein the population of lymphocytes is obtained by separating viable lymphocytes from a blood sample.

4. A process according to claim 3 wherein the blood donor is not known to be suffering from a disease.

5. A process according to claim 3 wherein the blood donor is in the early stages of cancer such that the blood donor is producing a large quantity of anti-cancer recognin antibody.

6. A process according to claim 1 which further comprises growing said lymphocytes in a cell culture.

7. A process according to claim 1 wherein the subpopulation selection comprises testing the lymphocyte culture media supernate for the presence of said anti-cancer recognin antibody.

8. A process according the claim 7 wherein the test for the presence of said anti-cancer recognin antibody comprises immunoabsorption of the antibody onto immobilized recognin antigen.

9. A process according to claim 1 wherein said treating step comprises adding an effective amount of pokeweed mitogen to the lymphocyte cell culture.

10. A process according to claim 9 wherein at least about 10 ug/ml of pokeweed mitogen are added to said lymphocyte cell culture.

11. A process according to claim 9 wherein about 20 ug/ml of pokeweed mitogen are added to said lymphocyte cell culture.

12. A process according to claim 1 wherein said treating step comprises transforming said lymphocyte cell subpopulation.

13. A process according to claim 12 wherein said subpopulation of lymphocytes are transformed by EB virus.

14. A process according to claim 1 which further comprises isolating the anti-cancer recognin antibody.

15. A process according to claim 14 wherein said isolation step comprises adsorbing said anti-cancer recognin antibody onto immobilized recognin.

16. A process according to claim 1 wherein the cancer recognin is malignin.

17. A human anti-cancer recognin antibody wherein said cancer recognin is derived from cancerous tumor tissue or cells, said recognin characterized by forming a single line precipitate with its specific antibody in quantitative precipitin tests and Ouchterlony gel diffusion tests, being soluble in water and aqueous solutions having a spectrophotometric absorption peak wave length of 280 mu and a molecular weight of from about 3,000 to about 25,000, and further characterized by having an amino acid residue composition characterized by high proportions of glutamic and aspartic acids and high ratios of glutamic and aspartic acids to histidine produced by a process comprising the steps of:

a) isolating a population of human lymphocyte cells;
   b) stimulating said isolated population of anti-cancer recognin antibody producing human lymphocytes in a manner effective to enhance anti-cancer recognin antibody production; and
   c) isolating the anti-cancer recognin antibody.

18. A product according to claim 17 wherein said product is human, fast-binding, anti-malignin antibody.

19. A product according to claim 17 wherein said product is human, slow-binding, anti-malignin antibody.

20. A process according to claim 14 which further comprises modifying the isolated anti-cancer recognin antibody by adding a chemotherapeutic agent to said antibody.

21. A human anti-cancer recognin antibody wherein said cancer recognin is derived from cancerous tumor tissue or cells, said recognin characterized by forming a single line precipitate with its specific antibody in quantitative precipitin tests and Ouchterlony gel diffusion tests, being soluble in water and aqueous solutions having a spectrophotometric absorption peak wave length of 280 mu and a molecular weight of from about 3,000 to about 25,000, and further characterized by having an amino acid residue composition characterized by high proportions of glutamic and aspartic acids and high ratios of glutamic and aspartic acids to histidine produced by a process comprising the steps of:

a) isolating a population of human lymphocyte cells;

b) stimulating said isolated population of anti-cancer recognin antibody producing human lymphocytes in a manner effective to enhance anti-cancer recognin antibody production;

c) isolating the anti-cancer recognin antibody; and d) modifying the isolated anti-cancer recognin antibody by adding a chemotherapeutic agent to said antibody.

22. A process according to claim 14 which further comprises modifying said isolated anti-cancer recognin antibody by adding a signal emitter to said antibody.

23. A human anti-cancer recognin antibody wherein said cancer recognin is derived from cancerous tumor tissue or cells, said recognin characterized by forming a single line precipitate with its specific antibody in quantitative precipitin tests and Ouchterlony gel diffusion tests, being soluble in water and aqueous solutions having a spectrophotometric absorption peak wave length of 280 mu and a molecular weight of from about 3,000 to about 25,000, and further characterized by having an amino acid residue composition characterized by high proportions of glutamic and aspartic acids and high ratios of glutamic and aspartic acids to histidine produced by a process comprising the steps of:

a) isolating a population of human lymphocyte cells;

b) stimulating said isolated population of anti-cancer recognin antibody producing human lymphocytes in a manner effective to enhance anti-cancer recognin antibody production;

c) isolating the anti-cancer recognin antibody; and d) adding a signal emitter to said antibody.

24. A process according to claim 22 wherein said signal emitter is fluorescent.

25. A process according to claim 22 wherein said signal emitter creates a radiological contrast image in a tissue environment.

26. A process according to claim 22 wherein said signal emitter is a nuclear magnetic resonance spin label.

27. A composition comprising human monoclonal anti-malignin antibody-FAST or a purified fragment thereof, whereby said antibody or a purified fragment thereof attaches to cancerous cells, said cells comprising malignin; and can thereby be detected by visible or signal-emitting means attached to said antibody, said malignin being derived from brain tumor cells, and which forms a single line precipitate with its specific antibody in quantitative precipitin tests and Ouchterlony gel diffusion tests, being soluble in water and aqueous solution having an acid or neutral pH, and insoluble at an alkaline pH, and has a spectrophotometric absorption peak wave length of 280 mu, a molecular weight of about 10,000, and an amino acid composition approximately as follows:

|  | APPROXIMATE NO. OF RESIDUES % |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 | ammonia and the amino acids cysteic, hydroxyproline, norleucine, isodesmosine, lysinonorleucine and gamma-aminobutyric acid being absent in detectable amounts.

28. A composition comprising human monoclonal anti-malignin antibody-FAST or a purified fragment thereof according to claim 27 wherein said antibody is predominantly IgM.

29. A composition comprising human monoclonal anti-malignin antibody-SLOW or a purified fragment thereof, whereby said antibody or a purified fragment thereof attaches to cancerous cells, said cells comprising malignin; and can thereby be detected by visible or signal-emitting means attached to said antibody, said malignin being derived from brain tumor cells, and which forms a single line precipitate with its specific antibody in quantitative precipitin tests and Ouchterlony gel diffusion tests, being soluble in water and aqueous solution having an acid or neutral pH, and insoluble at an alkaline pH, and has a spectrophotometric absorption peak wave length of 280 mu, a molecular weight of about 10,000, and an amino acid composition approximately as follows:

|  | APPROXIMATE NO. OF RESIDUES |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| 1/2 Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
|  | 89 | ammonia and the amino acids cysteic, hydroxyproline, norleucine, isodesmosine, lysinonorleucine and gamma-aminobutyric acid being absent in detectable amounts.

30. A composition comprising human monoclonal anti-malignin antibody-SLOW or a purified fragment thereof according to claim 27 wherein said antibody is predominantly IgM.

31. A composition comprising human monoclonal anti-malignin antibody-FAST and SLOW or a purified fragment thereof, whereby said antibody is cytotoxic to and kills cancer cells, said cells comprising malignin, whereby said antibody or a purified fragment thereof attaches to cancerous cells and can thereby be detected by visible or signal-emitting means attached to said antibody, said malignin being derived from brain tumor cells, and which forms a single line precipitate with its specific antibody in quantitative precipitin tests and Ouchterlony gel diffusion tests, being soluble in water and aqueous solution having an acid or neutral pH, and insoluble at a alkaline pH, and has a spectrophotometric absorption peak wave length of 280 mu, a molecular weight of about 10,000, and an amino acid composition approximately as follows:

| | APPROXIMATE NO. OF RESIDUES |
|---|---|
| Aspartic Acid | 9 |
| Threonine | 5 |
| Serira | 5 |
| Glutamic Acid | 13 |
| Prolina | 4 |
| Glycine | 6 |
| Alanine | 7 |
| Valine | 6 |
| 1/2 Cysteine | 1 |
| Methionine | 2 |
| Isoleucina | 4 |
| Leucine | 8 |
| Tyrosine | 3 |
| Phenylalanine | 3 |
| Lysine | 6 |
| Histidine | 2 |
| Arginine | 5 |
| | 89 | ammonia and the amino acids cysteic, hydroxyproline, norleucine, isodesmosine, lysinonorleucine and gamma-aminobutyric acid being absent in detectable amounts.

32. A composition according to claim 31 wherein said antibodies are predominantly IgM.

33. A cell line comprising a cell wherein said cell produces monoclonal anti-malignin antibody, all of the ancestors of said cell are selected from the group consisting of human cells, cells derived only from human cells and combinations thereof and said cell is not a hybridoma.

34. A cell line according to claim 33 wherein said cell has the normal appearance of a lymphocyte.

35. A cell line according to claim 34 wherein said cell has the appearance of a human lymphocyte.

36. A cell line according to claim 33 wherein said cell is a transformed cell.

37. A cell line according to claim 35 wherein said cell is virally transformed.

38. A cell line according to claim 36 wherein said cell is transformed by EB virus.

39. A cell line comprising:
a cell which produces monoclonal anti-malignin antibody, wherein all of the ancestors of said cell are selected from the group consisting of human cells, cells derived only from human cells, and combinations thereof, and said cell is not a hybridoma, said cell has the normal appearance of a human lymphocyte, and said cell produces human monoclonal anti-malignin antibody-FAST or a fragment thereof, wherein said antibody or fragment thereof attaches to cancerous cells that comprise human brain tumor-derived malignin, wherein said antibody is (1) detectable by visible or signal-emitting means attached to the antibody, (2) forms a single line precipitate with its target in quantitative precipitin tests and Ouchterlony diffusion tests, (3) is soluble in water and aqueous solution having an acid or neutral pH, (4) is insoluble at an alkaline pH, (5 has a spectrophotometric absorption peak wave length at 280 mu, (6) has a molecular weight of about 10,000 Daltons, and (7) has an amino acid composition approximately as follows:

| APPROXIMATE NO. OF RESIDUES | |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| 1/2 Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| | 89 | wherein
ammonia and cysteic acid, hydroxyproline, norleucine, isodesmosine, lysinorleucine and gamma-amino butyric acid are not detected, and wherein said antibody is predominantly IgM.

40. A cell line comprising a cell
a cell which produces monoclonal anti-malignin antibody, wherein all of the ancestors of said cell are selected from the group consisting of human cells, cells derived only from human cells, and combinations thereof, and said cell is not a hybridoma, said cell has the normal appearance of a human lymphocyte, and said cell produces human monoclonal anti-malignin antibody-SLOW or a fragment thereof, wherein said antibody or fragment thereof attaches to cancerous cells that comprise human brain tumor-derived malignin, wherein said antibody is (1) detectable by visible or signal-emitting means attached to the antibody, (2) forms a single line precipitate with its target in quantitative precipitin tests and Ouchterlony diffusion tests, (3) is soluble in water and aqueous solution having an acid or neutral pH, (4) is insoluble at an alkaline pH, (5) has a spectrophotometric absorption peak wave length at 280 mu, (6) has a molecular weight of about 10,000 Daltons, and (7) has an amino acid composition approximately as follows:

| APPROXIMATE NO. OF RESIDUES | |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |

-continued

| APPROXIMATE NO. OF RESIDUES | |
|---|---|
| Valine | 6 |
| 1/2 Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| | 89 | wherein
ammonia and cysteic acid, hydroxyproline, norleucine, isodesmosine, lysinorleucine and gamma-amino butyric acid are not detected, and wherein said antibody is predominantly IgM.

41. A cell line wherein said cell produces the composition of claim 32.

42. A composition comprising the nucleic acids of a cell according to claim 33.

43. A composition comprising the nucleic acids of a cell according to claim 34.

44. A composition comprising the nucleic acids of a cell according to claim 35.

45. A composition comprising the nucleic acids of a cell according to claim 36.

46. A composition comprising the nucleic acids of a cell according to claim 37.

47. A composition comprising the nucleic acids of a cell according to claim 38.

48. A composition comprising the nucleic acids of a cell according to claim 39.

49. A composition comprising the nucleic acids of a cell according to claim 40.

50. A composition comprising the nucleic acids of a cell according to claim 41.

51. A human lymphocyte recognin antibody according to claim 17 wherein said antibody inhibits target cell growth at femtomolar concentration.

52. The composition according to claim 31 wherein the human monoclonal anti-malignin antibody or fragment thereof inhibits target cell growth at femtomolar concentration.

53. The cell line according to claim 33 wherein the monoclonal anti-malignin antibody produced thereby inhibits the growth of target cells at femtomolar concentration.

54. A genetically human, anti-malignin monoclonal antibody which exhibits target cell cytotoxicity at picogram per cancer cell amount.

55. A non-hybridoma transformed cell line wherein said cell line produces a genetically human, anti-malignin antibody which exhibits target cell cytotoxicity at picogram per cancer cell amount.

56. The cell line according to claim 55 wherein the cell line consists of transformed human lymphocytes.

57. A composition comprising a genetically human, anti-malignin monoclonal antibody which exhibits target cell cytotoxicity at picogram per cancer cell amount and a pharmaceutically acceptable excipient.

* * * * *

UNITED STATES PATENT AND TRADEMARK OFFICE
CERTIFICATE OF CORRECTION

PATENT NO. : 5,866,690  
DATED : February 2, 1999  
INVENTOR(S) : Samuel Bogoch

Page 1 of 2

It is certified that error appears in the above-identified patent and that said Letters Patent is hereby corrected as shown below:

| Column | Line | |
|---|---|---|
| 8 | 40 | Change "section" to --sections--. |
| 9 | 8 | Change "infection" to --injection--. |
| 9 | 53 | Change "en" to --an--. |
| 11 | 51 | After "products" delete "a". |
| 11 | 18 | Change "solution):" to --(solutions):--. |
| 14 | 30 | Unter the column heading "Approximate Number of Residues" for "Valine" insert --4--. |
| 14 | 35 | Insert the number of residues for Phenylalanine: --3--. |
| 16 | 26 | Change "Glyine" to --Glycine--. |
| 17 | 67 | Change "end" to --and--. |
| 24 | 55 | Change "ware" to --were--. |
| 28 | 59 | Change "canner" to --cancer--. |
| 30 | Table II | Change "Cvary" to --Ovary--. |
| 31 | Table II | Before "(Sarcoma)" insert --Melanoma--. |
| 31 | Table III | Change "1'64" to --64--. |
| 34 | 23 | Change "<500" to -->500--. |
| 37 | 10 | Change "280 as" to --280 mµ--. |

UNITED STATES PATENT AND TRADEMARK OFFICE
CERTIFICATE OF CORRECTION

PATENT NO.  : 5,866,690
DATED       : February 2, 1999
INVENTOR(S) : Samuel Bogoch It is certified that error appears in the above-identified patent and that said Letters Patent is hereby corrected as shown below:

| Column | Line | |
|---|---|---|
| 37 | | TABLE Col. VIII: Change "7,1477" to --7,477--. |
| 42 | 33 | After "BALB/cJ" insert --mice--. |
| 42 | | 9 from bottom of TABLE: Move "27" from "MAMA-F" column to "CELLS" column. |
| 43 | 20 | Change "prod-aced" to --produced--. |
| 45 | 32 | After "usually" insert --arranged--. |
| 51 | 39 | Change "population" to --subpopulation--. |
| 52 | 3 | After "RESIDUES" delete "%". |
| 52 | 12 | Before "Cysteine" insert --1/2--. |

Signed and Sealed this

Eighteenth Day of January, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO. : 5,866,690
DATED : February 2, 1999
INVENTOR(S) : Samuel Bogoch

It is certified that error appears in the above-identified patent and that said Letters Patent is hereby corrected as shown below:

Column 22 line 41, change "lymphoma)" to -- (lymphoma)--.

Signed and Sealed this

Fourth Day of April, 2000

Attest:

Attesting Officer

Q. TODD DICKINSON

Director of Patents and Trademarks